(12) United States Patent
Steed et al.

(10) Patent No.: US 6,187,559 B1
(45) Date of Patent: Feb. 13, 2001

(54) PHOSPHOLIPASE D GENE

(75) Inventors: Paul Michael Steed, Bridgewater; Daniel James LaSala, Stirling, both of NJ (US)

(73) Assignee: Novartis AG, Basel (CH)

( * ) Notice: Under 35 U.S.C. 154(b), the term of this patent shall be extended for 0 days.

(21) Appl. No.: 09/141,206

(22) Filed: Aug. 28, 1998

Related U.S. Application Data

(60) Provisional application No. 60/057,802, filed on Aug. 28, 1997.

(51) Int. Cl.[7] .......................... C07H 21/04; C12N 15/85; C12N 1/20; C12N 15/63; C12N 15/00
(52) U.S. Cl. .......................... 435/69.1; 435/6; 435/325; 435/252.1; 536/23.1; 536/23.2; 536/23.5
(58) Field of Search .................. 435/6, 69.1, 325, 435/252.1; 536/23.1, 23.2, 23.5; 530/350

(56) References Cited

U.S. PATENT DOCUMENTS 5,859,222 * 1/1999 Leung et al. ......................... 536/23.2

OTHER PUBLICATIONS

Steed et al., database SPTREMBL on GenCore version 4.5, accession No. 014939, Jan. 1, 1998.*
Lopez et al., database SPTREMBL on GenCore version 4.5, accession No. 043540, Jun. 1, 1998.*
Billah, Current Opinion Immunology, vol. 5, No. 1, pp. 114–123 (1993).
Bollag et al., Endocrinology, vol. 127, No. 3, pp. 1436–1443 (1990).
Cockroft, Biochimica et Biophysica Acta, vol. 1113 pp. 135–160, (1992).
Colley et al., Current Biology, vol. 7, No. 3, pp. 191–201 (1997).
Dubyak et al., Biochem J., vol. 292, pp. 121–128 (1993).
Durieux et al., TIPS, vol. 14, pp. 249–254, (1993).
Exton, Biochemica et. Biophysics Acta, vol. 1212, pp. 26–42 (1994).
Hammondt et al., The Journal of Biological Chemistry, vol. 270, No. 50, pp. 29640–29643 (1995).
Jiang et al., Nature, vol. 378, pp. 409–412 (1995).
Kanoh et al., The Journal of Biological Chemistry, vol. 267, No. 35, pp. 25309–25314 (1992).
Kodaki et al., The Journal of Biological Chemistry, vol. 272, No. 17, pp. 11408–11413 (1997).
Okamura et al. J. Biol. Chem., vol. 269, Issue 49, pp. 31207–31213 (1994).
Lambeth et al., The Journal of Biological Chemistry, vol. 270, No. 6, pp. 2431–2434 (1995).
Metz et al., Biochem. J., vol. 270, pp. 427–435 (1990).
Pai et al., Anti Cancer Drug Design, vol. 9, pp. 363–372 Oxford University Pres. (1994).
Steed et al., (1996), Biochemistry, vol. 35, pp. 5229–5237 (1996).
Welsh et al., Biochemical and Biophysical Research Communications, vol. 202, No. 1, pp. 211–217 (1994).

* cited by examiner

*Primary Examiner*—George C. Elliott
*Assistant Examiner*—Sean McGarry
(74) *Attorney, Agent, or Firm*—David E. Wildman; Gregory D. Ferraro

(57) ABSTRACT

The invention relates to novel genes for human phospholipase D (PLD2), proteins produced by the gene, variants of PLD2, antibodies to the protein, assays using the protein and antibodies, and methods of treating PLD-dependent diseases using the compositions of the invention.

8 Claims, 1 Drawing Sheet

SEQUENCE LISTING

<160> NUMBER OF SEQ ID NOS: 8

<210> SEQ ID NO 1
<211> LENGTH: 3388
<212> TYPE: DNA
<213> ORGANISM: Human
<220> FEATURE:
<221> NAME/KEY: CDS
<222> LOCATION: (162)..(2963)
<223> OTHER INFORMATION: Human PLD2

<400> SEQUENCE: 1

```
ccatcctaat acgactcact atagggctcg agcggccgcc cgggcaggtc cggcccgct        60 tcggccggcc ccgcctcggc cggggcgtgg gctccggctg cagctccggt ctgctctctt      120
ggctcgggaa ccccgcggg cgctggctcc gtctgccagg g atg acg gcg acc cct       176
                                             Met Thr Ala Thr Pro
                                               1               5 gag agc ctc ttc ccc act ggg gac gaa ctg gac tcc agc cag ctc cag        224
Glu Ser Leu Phe Pro Thr Gly Asp Glu Leu Asp Ser Ser Gln Leu Gln
             10                  15                  20 atg gag tcc gat gag gtg gac acc ctg aag gag gga gag gac cca gcc        272
Met Glu Ser Asp Glu Val Asp Thr Leu Lys Glu Gly Glu Asp Pro Ala
         25                  30                  35 gac cgg atg cac ccg ttt ctg gcc atc tat gag ctt cag tct ctg aaa        320
Asp Arg Met His Pro Phe Leu Ala Ile Tyr Glu Leu Gln Ser Leu Lys
     40                  45                  50 gtg cac ccc ttg gtg ttc gca cct ggg gtc cct gtc aca gcc cag gtg        368
Val His Pro Leu Val Phe Ala Pro Gly Val Pro Val Thr Ala Gln Val
 55                  60                  65 gtg ggc acc gaa aga tat acc agc gga tcc aag gtg gga acc tgc act        416
Val Gly Thr Glu Arg Tyr Thr Ser Gly Ser Lys Val Gly Thr Cys Thr
 70                  75                  80                  85 ctg tat tct gtc cgc ttg act cac ggc gac ttt tcc tgg aca acc aag        464
Leu Tyr Ser Val Arg Leu Thr His Gly Asp Phe Ser Trp Thr Thr Lys
                 90                  95                 100 aag aaa tac cgt cat ttt cag gag ctg cat cgg gac ctc ctg aga cac        512
Lys Lys Tyr Arg His Phe Gln Glu Leu His Arg Asp Leu Leu Arg His
             105                 110                 115
```

-continued

| | |
|---|---|
| aaa gtc ttg atg agt ctg ctc cct ctg gct cga ttt gcc gtt gcc tat<br>Lys Val Leu Met Ser Leu Leu Pro Leu Ala Arg Phe Ala Val Ala Tyr<br>           120                   125                   130 | 560 |
| tct cca gcc cga gat gca ggc aac aga aag atg ccc tct cta ccc cgg<br>Ser Pro Ala Arg Asp Ala Gly Asn Arg Lys Met Pro Ser Leu Pro Arg<br>135                       140                     145 | 608 |
| gca ggt cct gag ggc tcc acc aga cat gca gcc agc aaa cag aaa tac<br>Ala Gly Pro Glu Gly Ser Thr Arg His Ala Ala Ser Lys Gln Lys Tyr<br>150                   155                   160                   165 | 656 |
| ctg gag aat tac ctc aac cgt ctc ttg acc atg tct ttc tat cgc aac<br>Leu Glu Asn Tyr Leu Asn Arg Leu Leu Thr Met Ser Phe Tyr Arg Asn<br>                 170                   175                   180 | 704 |
| tac cat gcc atg aca gag ttc ctg gaa gtc agt cag ctg tcc ttt atc<br>Tyr His Ala Met Thr Glu Phe Leu Glu Val Ser Gln Leu Ser Phe Ile<br>                185                   190                   195 | 752 |
| ccg gac ttg ggc cgc aaa gga ctg gag ggg atg atc cgg aag cgc tca<br>Pro Asp Leu Gly Arg Lys Gly Leu Glu Gly Met Ile Arg Lys Arg Ser<br>200                       205                   210 | 800 |
| ggt ggc cac cgt gtt cct ggc ctc acc tgc tgt ggc cga gac caa gtt<br>Gly Gly His Arg Val Pro Gly Leu Thr Cys Cys Gly Arg Asp Gln Val<br>          215                   220                   225 | 848 |
| tgt tat cgc tgg tcc aag aag tgg ctg gtg gtg aag gac tcc ttc ctg<br>Cys Tyr Arg Trp Ser Lys Lys Trp Leu Val Val Lys Asp Ser Phe Leu<br>230                       235                   240                   245 | 896 |
| ctg tac atg tgc ctc gag aca ggt gcc atc tca ttt gtt cag ctc ttt<br>Leu Tyr Met Cys Leu Glu Thr Gly Ala Ile Ser Phe Val Gln Leu Phe<br>                250                   255                   260 | 944 |
| gac cct ggc ttt gaa gtg caa gtg ggg aaa agg agc acg gaa gca cgg<br>Asp Pro Gly Phe Glu Val Gln Val Gly Lys Arg Ser Thr Glu Ala Arg<br>          265                   270                   275 | 992 |
| cac ggc gtg cgg atc gat acc tcc cac agg tcc ttg att ctc aag tgc<br>His Gly Val Arg Ile Asp Thr Ser His Arg Ser Leu Ile Leu Lys Cys<br>                280                   285                   290 | 1040 |
| agc agc tac cgg cag gca cgg tgg tgg gcc caa gaa atc act gag ctg<br>Ser Ser Tyr Arg Gln Ala Arg Trp Trp Ala Gln Glu Ile Thr Glu Leu<br>295                       300                   305 | 1088 |
| gca cag ggc cca ggc aga aac ttc cta cag ctg cac cgg cat gac agc<br>Ala Gln Gly Pro Gly Arg Asn Phe Leu Gln Leu His Arg His Asp Ser<br>310                       315                   320                   325 | 1136 |
| tac gcc cca ccc cgg cct ggg aac ttg gcc cgg tgg ttt gtg aat ggg<br>Tyr Ala Pro Pro Arg Pro Gly Asn Leu Ala Arg Trp Phe Val Asn Gly<br>                330                   335                   340 | 1184 |
| gca agt tac ttt gct gct gtg gca gat gcc atc ctt cga gct caa gag<br>Ala Ser Tyr Phe Ala Ala Val Ala Asp Ala Ile Leu Arg Ala Gln Glu<br>          345                   350                   355 | 1232 |
| gag att ttc atc aca gac tgg tgg ttg agt cct gag gtt tac ctg aag<br>Glu Ile Phe Ile Thr Asp Trp Trp Leu Ser Pro Glu Val Tyr Leu Lys<br>                360                   365                   370 | 1280 |
| cgt ccg gcc cat tca gat gac tgg aga ctg gac att atg ttc aag agg<br>Arg Pro Ala His Ser Asp Asp Trp Arg Leu Asp Ile Met Phe Lys Arg<br>375                       380                   385 | 1328 |
| aag gcg gag gaa ggt gtc cgt gtg tct att ctg ctg ttt aaa gaa gtg<br>Lys Ala Glu Glu Gly Val Arg Val Ser Ile Leu Leu Phe Lys Glu Val<br>390                       395                   400                   405 | 1376 |
| gaa ttg gcc ttg ggc atc aac agt ggc tat agc aag agg gcg ctg atg<br>Glu Leu Ala Leu Gly Ile Asn Ser Gly Tyr Ser Lys Arg Ala Leu Met<br>                410                   415                   420 | 1424 |
| ctg ctg cac ccc aac ata aag gtg atg cgt cac cca gac caa gtg acg<br>Leu Leu His Pro Asn Ile Lys Val Met Arg His Pro Asp Gln Val Thr | 1472 |

```
                         425                 430                 435
ttg tgg gcc cat cat gag aag ctc ctg gtg gtg gac caa gtg gta gca   1520
Leu Trp Ala His His Glu Lys Leu Leu Val Val Asp Gln Val Val Ala
        440                 445                 450 ttc ctg ggg gga ctg gac ctt gcc tat ggc cgc tgg gat gac ctg cac   1568
Phe Leu Gly Gly Leu Asp Leu Ala Tyr Gly Arg Trp Asp Asp Leu His
    455                 460                 465 tac cga ctg act gac ctt gga gac tct tct gaa tca gct gct tcc cag   1616
Tyr Arg Leu Thr Asp Leu Gly Asp Ser Ser Glu Ser Ala Ala Ser Gln
470                 475                 480                 485 ctt ccc acc ccg cgc cca gac tca cca gcc acc cca gac ttc ttt cac   1664
Leu Pro Thr Pro Arg Pro Asp Ser Pro Ala Thr Pro Asp Phe Phe His
            490                 495                 500 aac caa ttc ttc tgg ctg ggc aag gac tac agc aat ctt atc acc aag   1712
Asn Gln Phe Phe Trp Leu Gly Lys Asp Tyr Ser Asn Leu Ile Thr Lys
        505                 510                 515 gac tgg gtg cag ctg gac cgg cct ttc gaa gat ttc att gac agg gag   1760
Asp Trp Val Gln Leu Asp Arg Pro Phe Glu Asp Phe Ile Asp Arg Glu
    520                 525                 530 acg acc cct cgg atg cca tgg cgg gac gtt ggg gtg gtc gtc cat ggc   1808
Thr Thr Pro Arg Met Pro Trp Arg Asp Val Gly Val Val Val His Gly
535                 540                 545 cta ccg gcc cgg gac ctt gcc cgg cac ttc atc cag cgc tgg aat ttc   1856
Leu Pro Ala Arg Asp Leu Ala Arg His Phe Ile Gln Arg Trp Asn Phe
550                 555                 560                 565 acc aag acc acc agg gcc aag tac aag att ccc aca tac ccc tac ctg   1904
Thr Lys Thr Thr Arg Ala Lys Tyr Lys Ile Pro Thr Tyr Pro Tyr Leu
            570                 575                 580 ctt ccc aag ttt acc agc acg gcc aat cag ttc ccc ttc aca ctt cca   1952
Leu Pro Lys Phe Thr Ser Thr Ala Asn Gln Phe Pro Phe Thr Leu Pro
        585                 590                 595 gga ggg cag tgc acc acc gta cag gtc ttg cga tca gtg gac cgc tgg   2000
Gly Gly Gln Cys Thr Thr Val Gln Val Leu Arg Ser Val Asp Arg Trp
    600                 605                 610 tca gca ggg act ctg gag aac tcc atc ctc aat gcc tac ctg cac acc   2048
Ser Ala Gly Thr Leu Glu Asn Ser Ile Leu Asn Ala Tyr Leu His Thr
615                 620                 625 atc agg gag agc cag cac ttc ctc tac att gag aat cag ttc ttc att   2096
Ile Arg Glu Ser Gln His Phe Leu Tyr Ile Glu Asn Gln Phe Phe Ile
630                 635                 640                 645 agc tgc tca gat ggg cgg acg gtt ctg aac aag gtg ggc gat gag att   2144
Ser Cys Ser Asp Gly Arg Thr Val Leu Asn Lys Val Gly Asp Glu Ile
            650                 655                 660 gtg gac aga atc ctg aag gcc cac aaa cag ggg tgg tgt tac cga gtc   2192
Val Asp Arg Ile Leu Lys Ala His Lys Gln Gly Trp Cys Tyr Arg Val
        665                 670                 675 tac gtg ctt ttg ccc tta ctc cct ggc ttc gag ggt gac atc tcc acg   2240
Tyr Val Leu Leu Pro Leu Leu Pro Gly Phe Glu Gly Asp Ile Ser Thr
    680                 685                 690 ggc ggt ggc aac tcc atc cag gcc att ctg cac ttt act tac agg acc   2288
Gly Gly Gly Asn Ser Ile Gln Ala Ile Leu His Phe Thr Tyr Arg Thr
695                 700                 705 ctg tgt cgt ggg gag tat tca atc ctg cat cgc ctt aaa gca gcc atg   2336
Leu Cys Arg Gly Glu Tyr Ser Ile Leu His Arg Leu Lys Ala Ala Met
710                 715                 720                 725 ggg aca gca tgg cgg gac tat att tcc atc tgc ggg ctt cgt aca cac   2384
Gly Thr Ala Trp Arg Asp Tyr Ile Ser Ile Cys Gly Leu Arg Thr His
            730                 735                 740 gga gag ctg ggc ggg cac ccc gtc tcg gag ctc atc tac atc cac agc   2432
```

```
Gly Glu Leu Gly Gly His Pro Val Ser Glu Leu Ile Tyr Ile His Ser
            745                 750                 755 aag gtg ctc atc gca gat gac cgg aca gtc atc att ggt tct gca aac      2480
Lys Val Leu Ile Ala Asp Asp Arg Thr Val Ile Ile Gly Ser Ala Asn
        760                 765                 770 atc aat gac cgg agc ttg ctg ggg aag cgg gac agt gag ctg gcc gtg      2528
Ile Asn Asp Arg Ser Leu Leu Gly Lys Arg Asp Ser Glu Leu Ala Val
775                 780                 785 ctg atc gag gac aca gag acg gaa cca tcc ctc atg aat ggg gca gag      2576
Leu Ile Glu Asp Thr Glu Thr Glu Pro Ser Leu Met Asn Gly Ala Glu
790                 795                 800                 805 tat cag gcg ggc agg ttt gcc ttg agt ctg cgg aag cac tgc ttc ggt      2624
Tyr Gln Ala Gly Arg Phe Ala Leu Ser Leu Arg Lys His Cys Phe Gly
            810                 815                 820 gtg att ctt gga gca aat acc cgg cca gac ttg gat ctc cga gac ccc      2672
Val Ile Leu Gly Ala Asn Thr Arg Pro Asp Leu Asp Leu Arg Asp Pro
            825                 830                 835 atc tgt gat gac ttc ttc cag ttg tgg caa gac atg gct gag agc aac      2720
Ile Cys Asp Asp Phe Phe Gln Leu Trp Gln Asp Met Ala Glu Ser Asn
            840                 845                 850 gcc aat atc tat gag cag atc ttc cgc tgc ctg cca tcc aat gcc acg      2768
Ala Asn Ile Tyr Glu Gln Ile Phe Arg Cys Leu Pro Ser Asn Ala Thr
            855                 860                 865 cgt tcc ctg cgg act ctc cgg gag tac gtg gcc gtg gag ccc ttg gcc      2816
Arg Ser Leu Arg Thr Leu Arg Glu Tyr Val Ala Val Glu Pro Leu Ala
870                 875                 880                 885 acg gtc agt ccc ccc ttg gct cgg tct gag ctc acc cag gtc cag ggc      2864
Thr Val Ser Pro Pro Leu Ala Arg Ser Glu Leu Thr Gln Val Gln Gly
            890                 895                 900 cac ctg gtc cac ttc ccc ctc aag ttc cta gag gat gag tct ttg ctg      2912
His Leu Val His Phe Pro Leu Lys Phe Leu Glu Asp Glu Ser Leu Leu
            905                 910                 915 ccc ccg ctg ggt agc aag gag ggc atg atc ccc cta gaa gtg tgg aca      2960
Pro Pro Leu Gly Ser Lys Glu Gly Met Ile Pro Leu Glu Val Trp Thr
            920                 925                 930 tag ttgaggcccc cgtcagggag aggtcaccag ctgctgtgcc ccaccacgtc           3013
tggctccctg cccttaacc ccaaggactg agggcagtgc cctttgagat ctggggaggc    3073
aggcattcct gaagggaact agaggtgtta cagaggaccc ttacgtgaga aatagctgaa   3133
aagggcactc ccaaccctgg gctggggagg aggagagagt cccagagctc atccccctg    3193 ctgcccagtg caaaccactt ctccatgctg caaaggagaa gcacagctcc tgccaggtg    3253 agcagggtca agcctcttat tccaggagaa ggggctctgc cccaggccct actacccatt   3313
gttcccttcc tcttcctgcc cttgaacccc ctccctgtcc cagggccctc ccagcccatt   3373
gctgccaagg tggag                                                    3388

<210> SEQ ID NO 2
<211> LENGTH: 933
<212> TYPE: PRT
<213> ORGANISM: Human

<400> SEQUENCE: 2

Met Thr Ala Thr Pro Glu Ser Leu Phe Pro Thr Gly Asp Glu Leu Asp
1               5                   10                  15

Ser Ser Gln Leu Gln Met Glu Ser Asp Glu Val Asp Thr Leu Lys Glu
            20                  25                  30

Gly Glu Asp Pro Ala Asp Arg Met His Pro Phe Leu Ala Ile Tyr Glu
        35                  40                  45
```

```
Leu Gln Ser Leu Lys Val His Pro Leu Val Phe Ala Pro Gly Val Pro
     50                  55                  60
Val Thr Ala Gln Val Val Gly Thr Glu Arg Tyr Thr Ser Gly Ser Lys
 65                  70                  75                  80
Val Gly Thr Cys Thr Leu Tyr Ser Val Arg Leu Thr His Gly Asp Phe
                 85                  90                  95
Ser Trp Thr Thr Lys Lys Tyr Arg His Phe Gln Glu Leu His Arg
                100                 105                 110
Asp Leu Leu Arg His Lys Val Leu Met Ser Leu Leu Pro Leu Ala Arg
            115                 120                 125
Phe Ala Val Ala Tyr Ser Pro Ala Arg Asp Ala Gly Asn Arg Lys Met
        130                 135                 140
Pro Ser Leu Pro Arg Ala Gly Pro Glu Gly Ser Thr Arg His Ala Ala
145                 150                 155                 160
Ser Lys Gln Lys Tyr Leu Glu Asn Tyr Leu Asn Arg Leu Leu Thr Met
                165                 170                 175
Ser Phe Tyr Arg Asn Tyr His Ala Met Thr Glu Phe Leu Glu Val Ser
            180                 185                 190
Gln Leu Ser Phe Ile Pro Asp Leu Gly Arg Lys Gly Leu Glu Gly Met
        195                 200                 205
Ile Arg Lys Arg Ser Gly Gly His Arg Val Pro Gly Leu Thr Cys Cys
    210                 215                 220
Gly Arg Asp Gln Val Cys Tyr Arg Trp Ser Lys Lys Trp Leu Val Val
225                 230                 235                 240
Lys Asp Ser Phe Leu Leu Tyr Met Cys Leu Glu Thr Gly Ala Ile Ser
                245                 250                 255
Phe Val Gln Leu Phe Asp Pro Gly Phe Glu Val Gln Val Gly Lys Arg
            260                 265                 270
Ser Thr Glu Ala Arg His Gly Val Arg Ile Asp Thr Ser His Arg Ser
        275                 280                 285
Leu Ile Leu Lys Cys Ser Ser Tyr Arg Gln Ala Arg Trp Trp Ala Gln
    290                 295                 300
Glu Ile Thr Glu Leu Ala Gln Gly Pro Gly Arg Asn Phe Leu Gln Leu
305                 310                 315                 320
His Arg His Asp Ser Tyr Ala Pro Pro Arg Pro Gly Asn Leu Ala Arg
                325                 330                 335
Trp Phe Val Asn Gly Ala Ser Tyr Phe Ala Ala Val Ala Asp Ala Ile
            340                 345                 350
Leu Arg Ala Gln Glu Glu Ile Phe Ile Thr Asp Trp Trp Leu Ser Pro
        355                 360                 365
Glu Val Tyr Leu Lys Arg Pro Ala His Ser Asp Asp Trp Arg Leu Asp
    370                 375                 380
Ile Met Phe Lys Arg Lys Ala Glu Glu Gly Val Arg Val Ser Ile Leu
385                 390                 395                 400
Leu Phe Lys Glu Val Glu Leu Ala Leu Gly Ile Asn Ser Gly Tyr Ser
                405                 410                 415
Lys Arg Ala Leu Met Leu Leu His Pro Asn Ile Lys Val Met Arg His
            420                 425                 430
Pro Asp Gln Val Thr Leu Trp Ala His His Glu Lys Leu Leu Val Val
        435                 440                 445
Asp Gln Val Val Ala Phe Leu Gly Gly Leu Asp Leu Ala Tyr Gly Arg
    450                 455                 460
```

-continued

```
Trp Asp Asp Leu His Tyr Arg Leu Thr Asp Leu Gly Asp Ser Ser Glu
465                 470                 475                 480

Ser Ala Ala Ser Gln Leu Pro Thr Pro Arg Pro Asp Ser Pro Ala Thr
            485                 490                 495

Pro Asp Phe Phe His Asn Gln Phe Phe Trp Leu Gly Lys Asp Tyr Ser
        500                 505                 510

Asn Leu Ile Thr Lys Asp Trp Val Gln Leu Asp Arg Pro Phe Glu Asp
    515                 520                 525

Phe Ile Asp Arg Glu Thr Thr Pro Arg Met Pro Trp Arg Asp Val Gly
530                 535                 540

Val Val Val His Gly Leu Pro Ala Arg Asp Leu Ala Arg His Phe Ile
545                 550                 555                 560

Gln Arg Trp Asn Phe Thr Lys Thr Thr Arg Ala Lys Tyr Lys Ile Pro
            565                 570                 575

Thr Tyr Pro Tyr Leu Leu Pro Lys Phe Thr Ser Thr Ala Asn Gln Phe
        580                 585                 590

Pro Phe Thr Leu Pro Gly Gly Gln Cys Thr Thr Val Gln Val Leu Arg
    595                 600                 605

Ser Val Asp Arg Trp Ser Ala Gly Thr Leu Glu Asn Ser Ile Leu Asn
610                 615                 620

Ala Tyr Leu His Thr Ile Arg Glu Ser Gln His Phe Leu Tyr Ile Glu
625                 630                 635                 640

Asn Gln Phe Phe Ile Ser Cys Ser Asp Gly Arg Thr Val Leu Asn Lys
            645                 650                 655

Val Gly Asp Glu Ile Val Asp Arg Ile Leu Lys Ala His Lys Gln Gly
        660                 665                 670

Trp Cys Tyr Arg Val Tyr Val Leu Pro Leu Leu Pro Gly Phe Glu
    675                 680                 685

Gly Asp Ile Ser Thr Gly Gly Asn Ser Ile Gln Ala Ile Leu His
    690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
            725                 730                 735

Gly Leu Arg Thr His Gly Glu Leu Gly Gly His Pro Val Ser Glu Leu
        740                 745                 750

Ile Tyr Ile His Ser Lys Val Leu Ile Ala Asp Asp Arg Thr Val Ile
    755                 760                 765

Ile Gly Ser Ala Asn Ile Asn Asp Arg Ser Leu Leu Gly Lys Arg Asp
770                 775                 780

Ser Glu Leu Ala Val Leu Ile Glu Asp Thr Glu Thr Glu Pro Ser Leu
785                 790                 795                 800

Met Asn Gly Ala Glu Tyr Gln Ala Gly Arg Phe Ala Leu Ser Leu Arg
            805                 810                 815

Lys His Cys Phe Gly Val Ile Leu Gly Ala Asn Thr Arg Pro Asp Leu
        820                 825                 830

Asp Leu Arg Asp Pro Ile Cys Asp Asp Phe Phe Gln Leu Trp Gln Asp
    835                 840                 845

Met Ala Glu Ser Asn Ala Asn Ile Tyr Glu Gln Ile Phe Arg Cys Leu
850                 855                 860

Pro Ser Asn Ala Thr Arg Ser Leu Arg Thr Leu Arg Glu Tyr Val Ala
865                 870                 875                 880

Val Glu Pro Leu Ala Thr Val Ser Pro Pro Leu Ala Arg Ser Glu Leu
```

```
                    885                 890                 895
Thr Gln Val Gln Gly His Leu Val His Phe Pro Leu Lys Phe Leu Glu
                900                 905                 910

Asp Glu Ser Leu Leu Pro Pro Leu Gly Ser Lys Glu Gly Met Ile Pro
            915                 920                 925

Leu Glu Val Trp Thr
        930

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 3
tacaggaccc tgtgtcgtgg g                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 4
ctccaccttg gcagcaatgg                                                20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 5
ccgtgtgtac gaagcccgca gatgg                                          25

<210> SEQ ID NO 6
<211> LENGTH: 922
<212> TYPE: PRT
<213> ORGANISM: Human

<400> SEQUENCE: 6

Met Thr Ala Thr Pro Glu Ser Leu Phe Pro Thr Gly Asp Glu Leu Asp
 1               5                  10                  15

Ser Ser Gln Leu Gln Met Glu Ser Asp Glu Val Asp Thr Leu Lys Glu
            20                  25                  30

Gly Glu Asp Pro Ala Asp Arg Met His Pro Phe Leu Ala Ile Tyr Glu
        35                  40                  45

Leu Gln Ser Leu Lys Val His Pro Leu Val Phe Ala Pro Gly Val Pro
    50                  55                  60

Val Thr Ala Gln Val Val Gly Thr Glu Arg Tyr Thr Ser Gly Ser Lys
65                  70                  75                  80

Val Gly Thr Cys Thr Leu Tyr Ser Val Arg Leu Thr His Gly Asp Phe
                85                  90                  95

Ser Trp Thr Thr Lys Lys Lys Tyr Arg His Phe Gln Glu Leu His Arg
            100                 105                 110
```

-continued

```
Asp Leu Leu Arg His Lys Val Leu Met Ser Leu Leu Pro Leu Ala Arg
            115                 120                 125
Phe Ala Val Ala Tyr Ser Pro Ala Arg Asp Ala Gly Asn Arg Lys Met
130                 135                 140
Pro Ser Leu Pro Arg Ala Gly Pro Glu Gly Ser Thr Arg His Ala Ala
145                 150                 155                 160
Ser Lys Gln Lys Tyr Leu Glu Asn Tyr Leu Asn Gly Leu Leu Thr Met
            165                 170                 175
Ser Phe Tyr Arg Asn Tyr His Ala Met Thr Glu Phe Leu Glu Val Ser
            180                 185                 190
Gln Leu Ser Phe Ile Pro Asp Leu Gly Arg Lys Gly Leu Glu Gly Met
            195                 200                 205
Ile Arg Lys Arg Ser Gly Gly His Arg Val Pro Gly Leu Thr Cys Cys
210                 215                 220
Gly Arg Asp Gln Val Cys Tyr Arg Trp Ser Lys Arg Trp Leu Val Val
225                 230                 235                 240
Lys Asp Ser Phe Leu Leu Tyr Met Cys Leu Glu Thr Gly Ala Ile Ser
            245                 250                 255
Phe Val Gln Leu Phe Asp Pro Gly Phe Glu Val Gln Val Gly Lys Arg
            260                 265                 270
Ser Thr Glu Ala Arg His Gly Val Arg Ile Asp Thr Ser His Arg Ser
            275                 280                 285
Leu Ile Leu Lys Cys Ser Ser Tyr Arg Gln Ala Arg Trp Trp Ala Gln
            290                 295                 300
Glu Ile Thr Glu Leu Ala Gln Gly Pro Gly Arg Asp Phe Leu Gln Leu
305                 310                 315                 320
His Arg His Asp Ser Tyr Ala Pro Pro Arg Pro Gly Thr Leu Ala Arg
                325                 330                 335
Trp Phe Val Asn Gly Ala Gly Tyr Phe Ala Ala Val Ala Asp Ala Ile
            340                 345                 350
Leu Arg Ala Gln Glu Glu Ile Phe Ile Thr Asp Trp Trp Leu Ser Pro
            355                 360                 365
Glu Val Tyr Leu Lys Arg Pro Ala His Ser Asp Asp Trp Arg Leu Asp
370                 375                 380
Ile Met Phe Lys Arg Lys Ala Glu Glu Gly Val Arg Val Ser Ile Leu
385                 390                 395                 400
Leu Phe Lys Glu Leu Glu Leu Ala Leu Gly Ile Asn Ser Gly Tyr Ser
            405                 410                 415
Lys Arg Ala Leu Met Leu Leu His Pro Asn Ile Lys Val Met Arg His
            420                 425                 430
Pro Asp Gln Val Thr Leu Trp Ala His His Glu Lys Leu Leu Val Val
            435                 440                 445
Asp Gln Val Val Ala Phe Leu Gly Gly Leu Asp Leu Ala Tyr Gly Arg
450                 455                 460
Trp Asp Asp Leu His Tyr Arg Leu Thr Asp Leu Gly Asp Ser Ser Glu
465                 470                 475                 480
Ser Ala Ala Ser Gln Pro Pro Thr Pro Arg Pro Asp Ser Pro Ala Thr
            485                 490                 495
Pro Asp Leu Ser His Asn Gln Phe Phe Trp Leu Gly Lys Asp Tyr Ser
            500                 505                 510
Asn Leu Ile Thr Lys Asp Trp Val Gln Leu Asp Arg Pro Phe Glu Asp
            515                 520                 525
Phe Ile Asp Arg Glu Thr Thr Pro Arg Met Pro Trp Arg Asp Val Gly
```

-continued

```
            530                 535                 540
Val Val Val His Gly Leu Pro Ala Arg Asp Leu Ala Arg His Phe Ile
545                 550                 555                 560

Gln Arg Trp Asn Phe Thr Lys Thr Thr Lys Ala Lys Tyr Lys Thr Pro
                565                 570                 575

Thr Tyr Pro Tyr Leu Leu Pro Lys Ser Thr Ser Thr Ala Asn Gln Leu
                580                 585                 590

Pro Phe Thr Leu Pro Gly Gly Gln Cys Thr Thr Val Gln Val Leu Arg
                595                 600                 605

Ser Val Asp Arg Trp Ser Ala Gly Thr Leu Glu Asn Ser Ile Leu Asn
        610                 615                 620

Ala Tyr Leu His Thr Ile Arg Glu Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Lys Gln Gly
                660                 665                 670

Trp Cys Tyr Arg Val Tyr Val Leu Leu Pro Leu Leu Pro Gly Phe Glu
            675                 680                 685

Gly Asp Ile Ser Thr Gly Gly Gly Asn Ser Ile Gln Ala Ile Leu His
    690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
                725                 730                 735

Gly Leu Arg Thr His Gly Glu Leu Gly Gly His Pro Val Ser Glu Leu
            740                 745                 750

Ile Tyr Ile His Ser Lys Val Leu Ile Ala Asp Asp Arg Thr Val Ile
        755                 760                 765

Ile Gly Ser Ala Asn Ile Asn Asp Arg Ser Leu Leu Gly Lys Arg Asp
    770                 775                 780

Ser Glu Leu Ala Val Leu Ile Glu Asp Thr Glu Thr Glu Pro Ser Leu
785                 790                 795                 800

Met Asn Gly Ala Glu Tyr Gln Ala Gly Ser Val Ile Leu Gly Ala Asn
                805                 810                 815

Thr Arg Pro Asp Leu Asp Leu Arg Asp Pro Ile Cys Asp Asp Phe Phe
            820                 825                 830

Gln Leu Trp Gln Asp Met Ala Glu Ser Asn Ala Asn Ile Tyr Glu Gln
        835                 840                 845

Ile Phe Arg Cys Leu Pro Ser Asn Ala Thr Arg Ser Leu Arg Thr Leu
    850                 855                 860

Arg Glu Tyr Val Ala Val Glu Pro Leu Ala Thr Val Ser Pro Pro Leu
865                 870                 875                 880

Ala Arg Ser Glu Leu Thr Gln Val Gln Gly His Leu Val His Phe Pro
                885                 890                 895

Leu Lys Phe Leu Glu Asp Glu Ser Leu Leu Pro Pro Leu Gly Ser Lys
            900                 905                 910

Glu Gly Met Ile Pro Leu Glu Val Trp Thr
        915                 920

<210> SEQ ID NO 7
<211> LENGTH: 336
<212> TYPE: PRT
<213> ORGANISM: Human
```

<400> SEQUENCE: 7

```
Met Thr Ala Thr Pro Glu Ser Leu Phe Pro Thr Gly Asp Glu Leu Asp
  1               5                  10                  15
Ser Ser Gln Leu Gln Met Glu Ser Asp Glu Val Asp Thr Leu Lys Glu
             20                  25                  30
Gly Glu Asp Pro Ala Asp Arg Met His Pro Phe Leu Ala Ile Tyr Glu
         35                  40                  45
Leu Gln Ser Leu Lys Val His Pro Leu Val Phe Ala Pro Gly Val Pro
     50                  55                  60
Val Thr Ala Gln Val Val Gly Thr Glu Arg Tyr Thr Ser Gly Ser Lys
 65                  70                  75                  80
Val Gly Thr Cys Thr Leu Tyr Ser Val Arg Leu Thr His Gly Asp Phe
                 85                  90                  95
Ser Trp Thr Thr Lys Lys Lys Tyr Arg His Phe Gln Glu Leu His Arg
                100                 105                 110
Asp Leu Leu Arg His Lys Val Leu Met Ser Leu Leu Pro Leu Ala Arg
            115                 120                 125
Phe Ala Val Ala Tyr Ser Pro Ala Arg Asp Ala Gly Asn Arg Lys Met
130                 135                 140
Pro Ser Leu Pro Arg Ala Gly Pro Glu Gly Ser Thr Arg His Ala Ala
145                 150                 155                 160
Ser Lys Gln Lys Tyr Leu Glu Asn Tyr Leu Asn Gly Leu Leu Thr Met
                165                 170                 175
Ser Phe Tyr Arg Asn Tyr His Ala Met Thr Glu Phe Leu Glu Val Ser
                180                 185                 190
Gln Leu Ser Phe Ile Pro Asp Leu Gly Arg Lys Gly Leu Glu Gly Met
            195                 200                 205
Ile Arg Lys Arg Ser Gly Gly His Arg Val Pro Gly Leu Thr Cys Cys
            210                 215                 220
Gly Arg Asp Gln Val Cys Tyr Arg Trp Ser Lys Arg Trp Leu Val Val
225                 230                 235                 240
Lys Asp Ser Phe Leu Leu Tyr Met Cys Leu Glu Thr Gly Ala Ile Ser
                245                 250                 255
Phe Val Gln Leu Phe Asp Pro Gly Phe Glu Val Gln Val Gly Lys Arg
            260                 265                 270
Ser Thr Glu Ala Arg His Gly Val Arg Ile Asp Thr Ser His Arg Ser
            275                 280                 285
Leu Ile Leu Lys Cys Ser Ser Tyr Arg Gln Ala Arg Trp Trp Ala Gln
            290                 295                 300
Glu Ile Thr Glu Leu Ala Gln Gly Pro Gly Arg Asp Phe Leu Gln Leu
305                 310                 315                 320
His Arg His Asp Ser Tyr Ala Pro Pro Arg Pro Gly Thr Leu Ala Arg
                325                 330                 335
```

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Oligonucleotide Primer

<400> SEQUENCE: 8
gagctttctg gcttctgact cccctgacct ccttggcttg gcctccccc a         51

PHOSPHOLIPASE D GENE

CROSS-REFERENCE TO RELATED APPLICATION

This application claims the benefit under 35 U.S.C. §119 (e) of U.S. Provisional Application No. 60/057,802 filed Aug. 28, 1997.

FIELD OF THE INVENTION

The invention relates to novel genes for human phospholipase D (PLD2), proteins produced by the gene, variants of PLD2, antibodies to the protein, assays using the protein and antibodies, and methods of treating PLD-dependent diseases using the compositions of the invention.

BACKGROUND OF THE INVENTION

Various inflammatory and proliferative processes have been shown to be mediated through intracellular second messenger signaling associated with the activity of the Phospholipase D (PLD) enzyme.

PLD causes the hydrolysis of cell membrane phospholipids, such as the hydrolysis of phosphatidylcholine (PC), to phosphatidic acid (PA) and free choline. The hydrolysis of PC by PLD has been implicated in a variety of signal transduction pathways (Billah, M. M., (1993) Curr. Opin. Immunol. 5: 114–123; Exton, J. H., (1994) Biochem. Biophys. Acta 1212: 26–42). Phosphatidic acid (PA) has been implicated as a second messenger molecule which elicits biological responses such as enzyme release (Kanaho, et al., (1991) J. Immunol. 144: 1901–1908), the activation of protein kinase C (Stasek, Jr., et al., (1993) Biochem. Biophys. Res. Comm. 191: 134–141), activation of phospholipase C-γ (Jones and Carpenter, (1993) J. Biol. Chem. 268: 20845–20850), and cellular influx of calcium (Putney, et al., (1980) Nature 284: 345–347).

PLD has also been shown to stimulate the endogenous release of PA leading to increased insulin release from islet cells (Metz and Dunlop, (1990) Biochem. J. 270: 427–435) and aldosterone secretion from the adrenal glomerulosa cells (Bollag, et al., (1990) Endocrinology 127: 1436–1443). An endogenous choline pool for the biosynthesis of acetylcholine is created by the PLD mediated cleavage of choline from PC (Chalifour and Kanfer, (1980) Biophys. Biochem. Res. Comm. 124: 945–949).

Receptor-mediated activation of PLD occurs in cells treated with cytokines, growth factors, hormones, and neurotransmitters (Natarajan & Iwamoto, (1994) Biochem. Biophys. Acta 1213: 14–20, Zhou, et al., (1993) Biochem. Pharmacol. 46: 139–148). Many of these responses are dependent on trimeric guanyl nucleotide regulatory proteins (G proteins) (Cockcroft, S., (1992) Biochem. Biophys. Acta 1113: 135–160). PLD can be activated by tyrosine phosphorylation (Dubyak, et al., (1993) Biochem. J. 292: 121–128, Gomez-Cambronero, J., (1995) J. Interferon Cytokine Res. 15: 877–885), ceramides (Gomez-Munoz, et al., (1994) J. Biol. Chem. 269: 8937–8943), and by ras superfamily GTP binding proteins (Cockcroft, et al., (1994) Science 263: 523–526, Kuribara, et al., (1995) J. Biol. Chem. 270: 25667–25671, Lambeth, et al., (1995) J. Biol. Chem. 270: 2431–2434, Massenburg, et al., (1994) Proc. Natl. Acad. Sci. U.S.A. 91: 11718–11722).

In addition to producing the lipid messenger PA, PLD activity leads to the formation of diacylglycerol (DAG), the endogenous activator of PKC, through dephosphorylation of PA by the action of PA phosphohydrolase (Kanoh, et al., (1992) J. Biol. Chem. 267: 25309–25314). The release of DAG and associated activation of PKC in leukocytes can also lead to cell proliferation and inflammatory processes (Pfeffer, et al., (1990) Proc. Natl. Acad. Sci. U.S.A., 87: 6537–6541).

Mitogenic activity associated with PA and its metabolites has been linked to the actions of the arachidonic acid derivatives which are created from further metabolism of PA (Wilkes, et al., (1993) Fed. Eur. Biochem. Soc. (FEBS) 322: 147–150; Boarder, M. R. (1994) Trends Pharmacol. Sci. 15: 57–62), These arachidonic acid derivatives of PA have been shown to inhibit the conversion of the activated GTP-bound form of ras proteins to the inactivated form which is bound to GDP (Tsai, et al., (1989) Science, 243: 522–426). Recently studies have shown that an association with increased PLD activity and multidrug resistance in breast cancer cells (Welsh, et al., (1994) Biochem. Biophys. Res. Comm., 202: 211–217). PA and its metabolite, lysophosphatidic acid, have been shown to have growth factor-like mitogenic activity in fibroblast cultures (Durieux and Lynch, (1993) Trends Pharmacol. Sci. 14: 249–254). Thus the administration of PLD inhibitors would appear to offer a viable treatment for tumours and their proliferation.

Increased intracellular PA concentrations are manifested in a diversity of cellular changes in cell cycle control (McPhail, et al., (1993) Eur. J. Haematol. 51: 294–300; Stutchfield, et al., (1993) Biochem. J. 293: 649–655; Yasui, et al., (1994) J. Immunol. 152: 5922–5929), stimulation of DNA synthesis (Fukami and Takenawa, (1992) J. Biol. Chem. 267: 10988–10993), and stimulation of c-fos and c-myc transcription (Kanuss, et al., (1990) J. Biol. Chem. 269: 12228–12233).

Additionally, PLD signaling has been found to have a stimulatory effect on actin filamentation (Ha, et al., (1994) J. Cell. Biol. 123: 1789–1796). Actin rearrangements involve severing of actin filaments, formation of nucleation sites and subsequent re-polymerization. Such events are important for cellular activities such as mobility, proliferation, and secretion. Receptor-mediated activation of PLD in whole cell experiments has also been implicated in contraction (Ohanian, et al., (1990) J. Biol. Chem. 265: 8921–8928) and phagocytosis (Fallman, et al., (1992) J. Biol. Chem. 267: 2656–2663.

The release of PA has been linked to chemotaxis, degranulation and the generation of oxygen radicals in neutrophils and other inflammatory cells (I. M. Goldstein, Complement: Biologically Active Products. In *Inflammation: Basic Principles and Clinical Correlates*, 55 (J. I. Gallin, I. M. Goldstein, and R. Snyderman, eds., Raven Press, N.Y., N.Y., 1988). Chemoattractants such as C5a, N-formyl-methionyl-leucyl-phenylalanine (fMet-Leu-Phe) and leukotriene $B_4$ ($LTB_4$) bind to cell surface receptors to initiate intracellular events such as hydrolysis of membrane phospholipids by phospholipase C, phospholipase $A_2$, and PLD (Cockcroft, S. (1992) Biochem. Biophys. Act 11:13 135–160). Receptor stimulation in human polymorphonuclear neutrophils (PMN's), with C5a or fMet-Leu-Phe, has been shown to cause an increase in DAG predominantly as a result of PA dephosphorylation mediated by PLD (Billah, et al., (1989a) J. Biol. Chem. 264: 17069–17077; Mullmann, et al., (1990a) J. Immunol. 144: 1901–1908).

In the presence of ethanol and other short-chain alcohols, PLD catalyzes a transphosphatidylation reaction which results in the PA moiety from a phospholipid being transferred to the alcohol to produce phosphatidylethanol (PEt) (Kanfer, J. N., (1985) Can. J. Biochem. 58: 1370–1380). The formation of PEt from this reaction is widely utilized as a specific indicator of PLD activity in intact cells.

The addition of ethanol or butanol to intact cells has been shown to decrease PA production with a corresponding inhibition of secretion from mast cells (Gruchalla, et al., J. Immunol. (1990) 144: 2334–2342), platelets (Benistani and Rubin, (1990) Biochem. J. 269: 489–497), neutrophils (Yuli, et al., (1982) Proc. Natl. Acad. Sci. U.S.A. 79: 5906–5910), and differentiated HL60 cells.

Due to the lack of specific PLD inhibitors, the role of PLD activation in physiological processes, such as secretion and superoxide generation, has primarily been assessed by including primary alcohols such as ethanol or butanol into an in vitro assay to "trap" PLD generated product. In the presence of these alcohols, inhibition of free PA production is accompanied by a reduction of granule secretion or respiratory burst (Bauldry, et al., (1991) J. Biol. Chem. 266: 4173–4179); Bonser, et al., (1989) Biochem. J. 264: 617–620; Xie, et al., (1991) J. Clin. Invest. 88: 45–54; Stutchfield and Cockroft, (1993) Biochem. J. 293: 649–655; Zhou, et al., (1993) Biochem. Pharmacol. 46: 139–148). Recently, a ketoepoxide has been described which inhibited both PLD activation and superoxide generation induced by fMet-Leu-Phe in HL-60 granulocytes (Pai, et al., (1994) Anti-Cancer Drug Design 9: 363–372) lending further support for a role of PLD in the respiratory burst. Additionally, non-specific Inhibitors of PLD have been shown to decrease both fMet-Leu-Phe-induced superoxide production in HL-60 cells and platelet-derived growth factor-induced cellular growth in human fibrosarcoma cells (Pai, et al., (1994) Anti-Cancer Drug Design 9: 363–372).

Consistent with its critical role in second-messenger signaling, PLD is regulated by several mechanisms including protein phosphorylation (Dubyak et al., (1993) Biochem. J. 292:121–128), receptor-coupled G proteins (Cockroft, (1992) Biochem Biophys. Acta 1113:135–160), and small GTP binding proteins of the ras superfamily (Jiang et al., (1995) Nature 378:409–412; Lambeth et al., (1995) J. Biol. Chem. 270:2431–2434). Low molecular weight GTP-binding proteins of both the ADP-ribosylation factor (ARF) and Rho families have been shown to be required for maximal PLD activity. In addition to these regulatory components, it has been demonstrated that PLD activity is stimulated by gelsolin, a critical regulator of actin filamentation in a manner that is consistent with many observations regarding PLD signaling, inositol cycling, $Ca^{2+}$ influx, and cytoskeletal reorganizations (Steed et al., (1996) Biochemistry 35:5229–5237). Since Rho proteins have been shown to play a role in both PLD (Bowman et al., 1993) and cytoskeletal regulation (Leffers et al., (1993) Experimen. Cell Res. 209:165–174), this class of proteins is likely to be involved in the PLD/gelsolin interaction. A recent report indicates that PLD activation correlates with ARF translocation to the membrane, suggesting that ARF localizes PLD to the membrane (Houle et al., (1995) J. Biol. Chem. 270:22795–22800.

Despite the intensive study dedicated to PLD and its regulatory importance, the purification of a mammalian PLD to homogeneity and the cloning of human PLD have only been reported recently (Hammond et al., 1995, Okamura & Yamashita, 1994). The partial characterization of a second isoform of PLD, PLD2, has recently been reported (Colley et al., (1997) Current Biol. 7:191–201) for mice and rat (Tsutomu and Yamashita, (1997) J. Biol. Chem. 272(17):11406–11413). Mouse PLD2 affects the regulation of the cytoskeleton, is highly enriched in brain, is localized to the cell membrane, is negatively regulated, and has high constitutive activity. This is completely consistent with all of the characteristics of a PLD from rabbit brain (Steed et al., (1996) Biochemistry 35:5229–5237; Tsutomu and Yamashita, (1997) J. Biol. Chem. 272(17):11406–11413); therefore suggesting that rabbit brain PLD is possibly PLD2. Until now, the existence and identity of a PLD2 in humans has not been known. Surprisingly, a human PLD2 has been found and its amino acid sequence determined. Human PLD2 is the subject of the present invention.

SUMMARY OF THE INVENTION

One aspect of the present invention comprises a DNA sequence encoding a PLD2 protein having an amino acid sequence, wherein the amino acid sequence is at least about 90% sequence identical to SEQ ID NO. 2, preferably at least about 95% sequence identical to SEQ ID NO. 2, more preferably at least about 98% sequence identical to SEQ ID NO. 2.

Another aspect of the present invention comprises a DNA sequence that is at least about 90% sequence identical to SEQ ID NO. 1, preferably at least about 95% sequence identical to SEQ ID NO. 1, more preferably at least about 98% sequence identical to SEQ ID NO. 1.

Another aspect of the present invention comprises a protein having an amino acid sequence that is at least about 90% sequence identical to SEQ ID NO. 2, preferably at least about 95% sequence identical to SEQ ID NO. 2, more preferably at least about 98% sequence identical to SEQ ID NO. 2. Most preferably, the isolated protein has biological activity.

Another aspect of the present invention is directed to variants of the PLD2 protein. Preferred variants are hPLD2b and hPLD2c and the 75 kDa and 43 kDa variants shown in FIG. 1.

A further aspect of the present invention is a method for producing a PLD2 protein comprising:
 a) obtaining a DNA sequence encoding PLD2 protein;
 b) inserting said DNA into a host cell and expressing said PLD2 protein; and
 c) isolating said PLD2 protein.

A further aspect of the present invention is a method for diagnosing a PLD2 gene deficiency in a mammal comprising:
 a) obtaining a gene sample from the mammal;
 b) combining the gene sample with a portion of an isolated PLD2 polynucleotide under conditions of high stringency, wherein said portion is at least 8–20 nucleotides in length; and
 c) measuring the amount of hybridization between the gene sample and the isolated polynucleotide.

Preferably the portion of the polynucleotide is at least 50–100 nucleotides in length.

Another aspect of the present invention is an antibody which binds to PLD2 protein.

Such antibodies are useful in another aspect of the invention for the measurement of PLD2 protein levels in a mammal comprising:
 1) obtaining a sample from a mammal;
 2) incubating the sample with an anti-PLD2 antibody; and
 3) measuring the level of bound anti-PLD2 antibody in the sample.

Another aspect of the present invention is a method for modulating the level of PLD2 in a mammal comprising modulating the level of active PLD2 protein in a mammal wherein said modulation is selected from the group consisting of increasing or decreasing the level of active PLD2 protein in said mammal. A preferred method for increasing the level of active protein in a mammal is by administration of a therapeutically effective amount of PLD2 protein, particularly by gene therapy. A preferred method for decreasing the level of active protein in a mammal is by administration of a therapeutically effective amount of an anti-PLD2 antibody, particularly by administration of a therapeutically effective amount of an antisense oligonucleotide against PLD2.

To further assist in the interpretation of the various embodiments of the present invention, the following definitions are provided to guide the practitioner of the present invention.

"Isolated" or "substantially pure" when referring to nucleic acids or proteins, refers to those nucleic acids and proteins that have been purified away form other cellular components and contaminants, i.e., lipids and/or proteins, by standard techniques, including, for example, alkaline/SDS treatment, CsCl banding, column chromatography, phenol/chloroform treatment, and other purification techniques known in the art. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

"Nucleic acid", "DNA sequence" or "polynucleotide" refers to a deoxyribonucleotide or ribonucleotide polymer in either single- or double stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequences thereof. A nucleic acid encodes another nucleic acid where it is the same as the specified nucleic acid, or complementary to the specified nucleic acid.

"Identical", "sequence identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) Gene 73:237–244 and Higgins and Sharp (1989)CABIOS 5:151–153; Corpet et al. (1988) Nucleic Acids Res. 16:10881–10890; Huang et al (1992) Computer Applications in the Biosciences 8:155–165; and Pearson et al. (1994) Methods in molecular Biology 24:307–331. Alignment is also often performed by inspection and manual alignment.

"Sequence identical polynucleotide or amino acid sequences" means that a polynucleotide or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Selectively hybridizing" or "selective hybridization" includes hybridization, under stringent hybridization conditions, of a nucleic acid sequence to a specified nucleic acid target sequence to a detectably greater degree that its hybridization to non-target nucleic acid sequences. Selectively hybridizing sequences have at least 90% sequence identity, preferably 95% sequence identity, and most preferably 98–100% sequence identity (i.e., complementarity) with each other.

"Stringent hybridization" conditions or "stringent conditions" in the context of nucleic acid hybridization assay formats are sequence dependent, and are different under different environmental parameters. An extensive guide to hybridization of nucleic acids is found in Tijssen (1993) *Laboratory Techniques in Biochemistry and Molecular Biology—Hybridization with Nucleic Acid Probes* Part 1, Chapter 2 "Overview of Principles of Hybridization and the Strategy of Nucleic Acid Probe Assays" Elsevier, New York. Generally, highly stringent conditions are selected to be about 5° C. lower than the thermal melting point $T_m$ for the specific sequence at a defined ionic strength and pH. The $T_m$ is the temperature (under defined ionic strength and pH) at which 50% of the target sequence hybridizes to a perfectly matched probe. Very stringent conditions are selected to be equal to the Tm point for a particular nucleic acid of the present invention, this occurs, e.g., when a copy of a nucleic acid is created using the maximum codon degeneracy permitted by the genetic code. Stringent hybridization conditions are sequence-dependent and will be different in different circumstances. Longer sequences hybridize specifically at higher temperatures.

DETAILED DESCRIPTION OF THE INVENTION

Figures 1A, 1B:
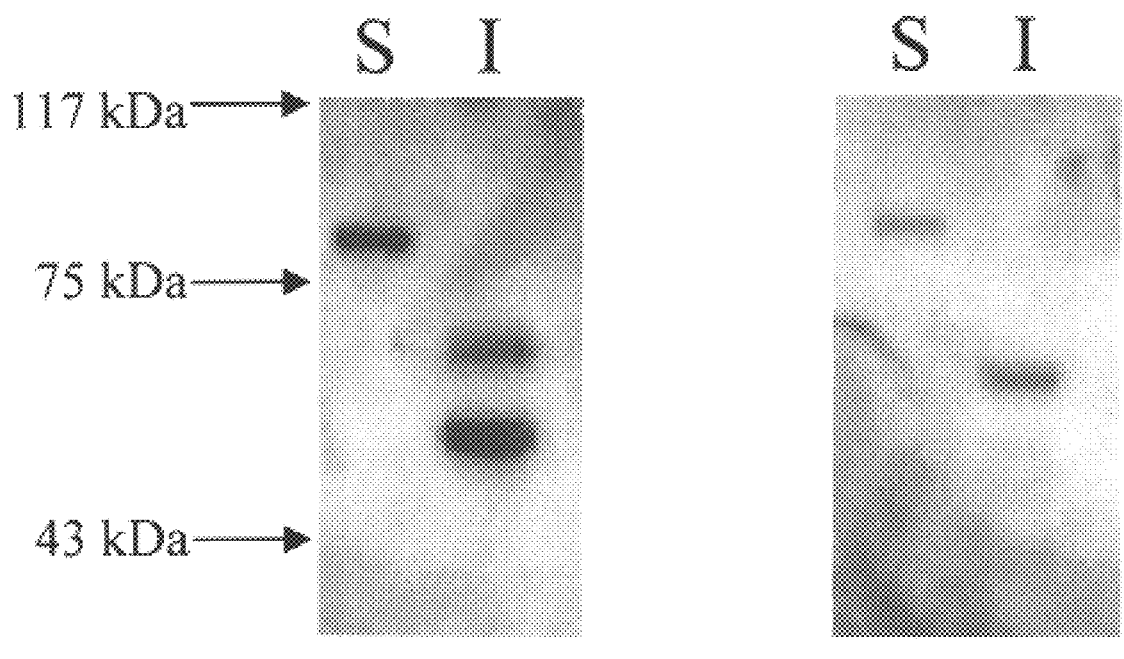
FIG. 1A illustrates the variants which result from the in vivo processing of PLD2 by cell line AIN4, a non-tumor breast cell line.
FIG. 1B illustrates the variants which results from the *in vivo* processing of PLD2 by cell line T47D, a breast tumor-like cell line. Both cell lines were fractionated with the detergent Triton X-100. Watts, R. G. (1995), Role of gelsolin in the formation and organization of triton-soluble f-actin during myeloid differentiation of HL-60 cells. Blood 85(8): 2212–2221. Triton soluble (S) and insoluble fractions (I) were separated on SDS PAGE and a Western Blot was performed using standard methods with an anti-mPLD2 antibody (Quality Control Biochemicals Corporation, Homkinton Mass. U.S.A.) Blot was provided by Dr. H. Asch, Roswell Park Cancer Inst. New York, U.S.A.

Various aspects of the present invention are drawn to newly discovered isoforms of human phospholipase D ("PLD2") protein, newly discovered polynucleotides encoding PLD2, antibodies to PLD2 and methods for using these new polynucleotides, protein and antibodies.

Polynucleotides

The first aspect of the present invention relates to an isolated polynucleotide comprising a DNA sequence encoding a PLD2 protein having an amino acid sequence, wherein the amino acid sequence is at least 90% sequence identical to SEQ ID NO. 2. The term "polynucleotide encoding an polypeptide (protein)" encompasses a polynucleotide which includes only coding sequence for the polypeptide as well as a polynucleotide which includes additional coding and/or non-coding sequence. Preferably, the amino acid sequence is at least 95% sequence identical to SEQ ID NO. 2 and more preferably at least 98% sequence identical to SEQ ID NO. 2. Alternatively, the isolated polynucleotide of the invention comprises a DNA sequence that is at least about 90% sequence identical to SEQ ID NO. 1. Preferably, the polynucleotide comprises a DNA sequence that is at least 95% sequence identical to SEQ ID NO. 1, more preferably at least 98% sequence identical to SEQ ID NO. 1. The polynucleotides can be obtained by a variety of means. Smaller oligonucleotides can be synthesized chemically using known techniques. The oligonucleotides can also be synthesized using recombinant DNA technology by placing the appropriate DNA sequence in an expression system, expressing or amplifying the DNA or RNA produced and subsequently isolating the oligonucleotid. The oligonucleotides can be combined, using convenient restriction sites, with other genetic elements necessary for amplification, such as promoters, ribosome binding sites, etc. These techniques are well known and can be used to produce quantities of a desired oligonucleotide once the sequence of the oligonucletide is known.

The human phospholipase D2 cDNA sequence that was obtained was 3388 base pairs long as follows (SEQ ID NO. 1).

```
CCATCCTAAT ACGACTCACT ATAGGGCTCG AGCGGCCGCC CGGGCAGGTC CGGCCCCGCT   60    SEQ ID NO. 1

TCGGCCGGCC CCGCCTCGGC CGGGGCGTGG GCTCCGGCTG CAGCTCCGGT CTGCTCTCTT  120

GGCTCGGGAA CCCCCGCGGG CGCTGGCTCC GTCTGCCAGG GATGACGGCG ACCCCTGAGA  180

GCCTCTTCCC CACTGGGGAC GAACTGGACT CCAGCCAGCT CCAGATGGAG TCCGATGAGG  240

TGGACACCCT GAAGGAGGGA GAGGACCCAG CCGACCGGAT GCACCCGTTT CTGGCCATCT  300

ATGAGCTTCA GTCTCTGAAA GTGCACCCCT TGGTGTTCGC ACCTGGGGTC CCTGTCACAG  360

CCCAGGTGGT GGGCACCGAA AGATATACCA GCGGATCCAA GGTGGGAACC TGCACTCTGT  420

ATTCTGTCCG CTTGACTCAC GGCGACTTTT CCTGGACAAC CAAGAAGAAA TACCGTCATT  480

TTCAGGAGCT GCATCGGGAC CTCCTGAGAC ACAAAGTCTT GATGAGTCTG CTCCCTCTGG  540

CTCGATTTGC CGTTGCCTAT TCTCCAGCCC GAGATGCAGG CAACAGAAAG ATGCCCTCTC  600

TACCCCGGGC AGGTCCTGAG GGCTCCACCA GACATGCAGC CAGCAAACAG AAATACCTGG  660

AGAATTACCT CAACCGTCTC TTGACCATGT CTTTCTATCG CAACTACCAT GCCATGACAG  720

AGTTCCTGGA AGTCAGTCAG CTGTCCTTTA TCCCGGACTT GGGCCGCAAA GGACTGGAGG  780

GGATGATCCG GAAGCGCTCA GGTGGCCACC GTGTTCCTGG CCTCACCTGC TGTGGCCGAG  840

ACCAAGTTTG TTATCGCTGG TCCAAGAAGT GGCTGGTGGT GAAGGACTCC TTCCTGCTGT  900

ACATGTGCCT CGAGACAGGT GCCATCTCAT TTGTTCAGCT CTTTGACCCT GGCTTTGAAG  960

TGCAAGTGGG GAAAAGGAGC ACGGAAGCAC GGCACGGCGT GCGGATCGAT ACCTCCCACA 1020

GGTCCTTGAT TCTCAAGTGC AGCAGCTACC GGCAGGCACG GTGGTGGGCC CAAGAAATCA 1080

CTGAGCTGGC ACAGGGCCCA GGCAGAAACT TCCTACAGCT GCACCGGCAT GACAGCTACG 1140

CCCCACCCCG GCCTGGGAAC TTGGCCCGGT GGTTTGTGAA TGGGGCAAGT TACTTTGCTG 1200

CTGTGGCAGA TGCCATCCTT CGAGCTCAAG AGGAGATTTT CATCACAGAC TGGTGGTTGA 1260

GTCCTGAGGT TTACCTGAAG CGTCCGGCCC ATTCAGATGA CTGGAGACTG GACATTATGT 1320

TCAAGAGGAA GGCGGAGGAA GGTGTCCGTG TGTCTATTCT GCTGTTTAAA GAAGTGGAAT 1380

TGGCCTTGGG CATCAACAGT GGCTATAGCA AGAGGGCGCT GATGCTGCTG CACCCCAACA 1440
```

```
TAAAGGTGAT GCGTCACCCA GACCAAGTGA CGTTGTGGGC CCATCATGAG AAGCTCCTGG  1500

TGGTGGACCA AGTGGTAGCA TTCCTGGGGG GACTGGACCT TGCCTATGGC CGCTGGGATG  1560

ACCTGCACTA CCGACTGACT GACCTTGGAG ACTCTTCTGA ATCAGCTGCT TCCCAGCTTC  1620

CCACCCCGCG CCCAGACTCA CCAGCCACCC CAGACTTCTT TCACAACCAA TTCTTCTGGC  1680

TGGGCAAGGA CTACAGCAAT CTTATCACCA AGGACTGGGT GCAGCTGGAC CGGCCTTTCG  1740

AAGATTTCAT TGACAGGGAG ACGACCCCTC GGATGCCATG GCGGGACGTT GGGGTGGTCG  1800

TCCATGGCCT ACCGGCCCGG GACCTTGCCC GGCACTTCAT CCAGCGCTGG AATTTCACCA  1860

AGACCACCAG GGCCAAGTAC AAGATTCCCA CATACCCCTA CCTGCTTCCC AAGTTTACCA  1920

GCACGGCCAA TCAGTTCCCC TTCACACTTC CAGGAGGGCA GTGCACCACC GTACAGGTCT  1980

TGCGATCAGT GGACCGCTGG TCAGCAGGGA CTCTGGAGAA CTCCATCCTC AATGCCTACC  2040

TGCACACCAT CAGGGAGAGC CAGCACTTCC TCTACATTGA GAATCAGTTC TTCATTAGCT  2100

GCTCAGATGG GCGGACGGTT CTGAACAAGG TGGGCGATGA GATTGTGGAC AGAATCCTGA  2160

AGGCCCACAA ACAGGGGTGG TGTTACCGAG TCTACGTGCT TTTGCCCTTA CTCCCTGGCT  2220

TCGAGGGTGA CATCTCCACG GGCGGTGGCA ACTCCATCCA GGCCATTCTG CACTTTACTT  2280

ACAGGACCCT GTGTCGTGGG GAGTATTCAA TCCTGCATCG CCTTAAAGCA GCCATGGGGA  2340

CAGCATGGCG GGACTATATT TCCATCTGCG GGCTTCGTAC ACACGGAGAG CTGGGCGGGC  2400

ACCCCGTCTC GGAGCTCATC TACATCCACA GCAAGGTGCT CATCGCAGAT GACCGGACAG  2460

TCATCATTGG TTCTGCAAAC ATCAATGACC GGAGCTTGCT GGGGAAGCGG GACAGTGAGC  2520

TGGCCGTGCT GATCGAGGAC ACAGAGACGG AACCATCCCT CATGAATGGG GCAGAGTATC  2580

AGGCGGGCAG GTTTGCCTTG AGTCTGCGGA AGCACTGCTT CGGTGTGATT CTTGGAGCAA  2640

ATACCCGGCC AGACTTGGAT CTCCGAGACC CCATCTGTGA TGACTTCTTC CAGTTGTGGC  2700

AAGACATGGC TGAGAGCAAC GCCAATATCT ATGAGCAGAT CTTCCGCTGC CTGCCATCCA  2760

ATGCCACGCG TTCCCTGCGG ACTCTCCGGG AGTACGTGGC CGTGGAGCCC TTGGCCACGG  2820

TCAGTCCCCC CTTGGCTCGG TCTGAGCTCA CCCAGGTCCA GGGCCACCTG GTCCACTTCC  2880

CCCTCAAGTT CCTAGAGGAT GAGTCTTTGC TGCCCCCGCT GGGTAGCAAG GAGGGCATGA  2940

TCCCCCTAGA AGTGTGGACA TAGTTGAGGC CCCCGTCAGG GAGAGGTCAC CAGCTGCTGT  3000

GCCCCACCAC GTCTGGCTCC CTGCCCCTTA ACCCCAAGGA CTGAGGGCAG TGCCCTTTGA  3060

GATCTGGGGA GGCAGGCATT CCTGAAGGGA ACTAGAGGTG TTACAGAGGA CCCTTACGTG  3120

AGAAATAGCT GAAAAGGGCA CTCCCAACCC TGGGCTGGGG AGGAGGAGAG AGTCCCAGAG  3180

CTCATCCCCC CTGCTGCCCA GTGCAAACCA CTTCTCCATG CTGCAAAGGA GAAGCACAGC  3240

TCCTGCCAGG GTGAGCAGGG TCAAGCCTCT TATTCCAGGA GAAGGGGCTC TGCCCCAGGC  3300

CCTACTACCC ATTGTTCCCT TCCTCTTCCT GCCCTTGAAC CCCCTCCCTG TCCCAGGGCC  3360

CTCCCAGCCC ATTGCTGCCA AGGTGGAG                                    3388
```

The polynucleotide which encodes for the polypeptide of SEQ ID NO. 2 may include, but is not limited to: only the coding sequence for the polypeptide; the coding sequence for the polypeptide and additional coding sequence such as a leader sequence or a proprotein sequence; the coding sequence for the polypeptide (and optionally additional coding sequence) and non-coding sequence, such as introns or non-coding sequence 5' and/or 3' of the coding sequence for the polypeptide.

Thus, the term "polynucleotide encoding an polypeptide (protein)", encompasses a polynucleotide which includes only coding sequence for the polypeptide as well as a polynucleotide which includes additional coding and/or non-coding sequence.

The present invention further relates to fragments and variants of the hereinabove described polynucleotides which encode for fragments, analogs and derivatives of the polypeptide having the deduced amino acid sequence of SEQ ID NO. 2. The variants of the polynucleotide may be a naturally occurring allelic variant of the polynucleotide or a non-naturally occurring variant of the polynucleotide. Fragments may be a portion of the reference polynucleotide SEQ ID NO. 1, comprising as few as at least 15, 30, 45, 60, 80, 100 or more nucleotides, preferably at least 115, 130, 145, 170 or more nucleotides, more preferably at least 200, 250, 300, 400, 500 or more nucleotides, even more preferably at least 600, 800, 900 or more nucleotides.

Thus, the present invention includes polynucleotides encoding the same polypeptide as shown in SEQ ID NO. 2 as well as variants of such polynucleotides which variants encode for a fragment, derivative or analog of the polypeptide of SEQ ID NO. 2. Such nucleotide variants include deletion variants, substitution variants and addition or insertion variants.

As hereinabove indicated, the polynucleotide may have a coding sequence which is a naturally occurring allelic variant of the coding sequence shown in SEQ ID NO. 1. As known in the art, an allelic variant is an alternate form of a polynucleotide sequence which may have a substitution, deletion or addition of one or more nucleotides, which does not substantially alter the function of the encoded polypeptide. Preferred allelic variants are polynucleotides which encode the 43 and 75 kDa variants as shown in FIG. 1 and polynucleotides as described in Example 3 herein that encode two splice variants hPLD2b (SEQ ID NO. 6) and hPLD2c (SEQ ID NO. 7) and polynucleoitde sequences that are at least 90% sequence identical, more preferably at least 95% sequence identical and most preferably at least 98% sequence identical to the allelic variant polynucleotides.

The present invention also includes polynucleotides, wherein the coding sequence for the polypeptide may be fused in the same reading frame to a polynucleotide sequence which aids in expression and secretion of a polypeptide from a host cell, for example, a leader sequence which functions to control transport of an polypeptide from the cell. The polypeptide having a leader sequence is a preprotein and may have the leader sequence cleaved by the host cell to form the form of the polypeptide. The polynucleotides may also encode for a proprotein which is the protein plus additional 5' amino acid residues. A protein having a prosequence is a proprotein and is an inactive form of the protein. Once the prosequence is cleaved an active protein remains.

PLD2 Protein

A second aspect of the present invention is an isolated protein comprising a protein having an amino acid sequence that is at least about 90% sequence identical to SEQ ID NO. 2 as well as fragments, analogs and derivatives of such polypeptide. The terms "fragment," "derivative" and "analog" when referring to the polypeptide of FIG. 5 (SEQ ID NO. 2) means a polypeptide which retains essentially the same biological function or activity as such polypeptide.

Thus, an analog includes a proprotein which can be activated by cleavage of the proprotein portion to produce an active polypeptide. The fragments, derivatives or analogs of the polypeptide of SEQ ID NO. 2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the polypeptide or a proprotein sequence. Such fragments, derivatives and analogs are deemed to be within the scope of those skilled in the art from the teachings herein.

A variant, i.e. a "fragment", "analog" or "derivative" polypeptide, and reference polypeptide may differ in amino acid sequence by one or more substitutions, additions, deletions, fusions and truncations, which may be present in any combination. Among preferred variants are those that vary from a reference by conservative amino acid substitutions. Such substitutions are those that substitute a given amino acid by another amino acid of like character. Conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies. Preferred variants are the two splice variants or allelic variants hPLD2b (SEQ ID NO. 6), hPLD2c (SEQ ID NO. 7) and the 43 kDa and 75 kDa variants shown in FIG. 1 and amino acid sequences that are at least 90% sequence identical, more preferably at least 95% sequence identical and most preferably at least 98% sequence identical to SEQ ID NOS. 6 or 7. The 43 kDa and 75 kDa variants shown in FIG. 1 provide evidence that PLD2 is clearly processed because the full-length (116 kDa) hPLD2 under the column labeled (I). It has also been unexpectedly found that these two variants have altered subcellular localization and the processing of full-length PLD2 in vivo appears to be aberrant in tumor-like cells Preferably, the isolated protein has an amino acid sequence that is at least 95% sequence identical to SEQ ID NO. 2, more preferably at least 98% sequence identical to SEQ ID NO. 2. Most preferably, the isolated protein has PLD2 biological activity, especially when the biological activity is activity in a PLD assay.

The PLD2 protein can be obtained by a variety of means. Smaller peptides (less than 50 amino acids long) may be conveniently synthesized by standard chemical techniques. PLD2 may also be purified from biological sources by methods well known in the art (*Protein Purification, Principles and Practice*, second edition (1987) Scopes, Springer Verlag, N.Y.). They may also be produced in their naturally occurring, truncated, or fusion protein forms by recombinant DNA technology using techniques well known in the art. These methods include, for example, in vitro recombinant DNA techniques, synthetic techniques and in vivo genetic recombination. See, for example, the techniques described in Sambrook et al. (1989) *Molecular Cloning, A laboratory Manual*, Cold Spring Harbor Press, N.Y.; and Ausubel et al., eds. (1989) *Current Protocols in Molecular Biology*, Green Publishing Associates, Inc., and John Wiley & Sons, Inc., N.Y. Alternatively, RNA encoding the proteins may be chemically synthesized. See, for example, the techniques described in *Oligonucleotide Synthesis*, (1984) Gait ed., IRL Press, Oxford, which is incorporated by reference herein in its entirety. Obtaining large quantities of PLDs is preferably by recombinant techniques as further described herein. Therefore, a further aspect of the present invention relates to the recombinant production of PLD2.

The coding region for the hPLD2 protein was coded for by the region 162–2963 of the cDNA sequence and its amino acid sequence is shown in SEQ ID NO. 2.

```
ThrAlaThrProGluSerLeuPheProThrGlyAspGluLeuAspSerSerGlnLeuGlnMetGluSerAspGluValAspThrLeuLys  SEQ ID NO. 2

GluGlyGluAspProAlaAspArgMetHisProPheLeuAlaIleTyrGluLeuGlnSerLeuLysValHisProLeuValPheAlaPro

GlyValProValThrAlaGlnValValGlyThrGluArgTyrThrSerGlySerLysValGlyThrCysThrLeuTyrSerValArgLeu

GlyAspPheSerTrpThrThrLysLysLysTyrArgHisPheGlnGluLeuHisArgAspLeuLeuArgHisLysValLeuMetSerLeu

LeuProLeuAlaArgPheAlaValAlaTyrSerProAlaArgAspAlaGlyAsnArgLysMetProSerLeuProArgAlaGlyProGlu

GlySerThrArgHisAlaAlaSerLysGlnLysTyrLeuGluAsnTyrLeuAsnGlyLeuLeuThrMetSerPheTyrArgAsnTyrHis

AlaMetThrGluPheLeuGluValSerGlnLeuSerPheIleProAspLeuGlyArgLysGlyLeuGluGlyMetIleArgLysArgSer

GlyGlyHisArgValProGlyLeuThrCysCysGlyArgAspGlnValCysTyrArgTrpSerLysArgTrpLeuValValLysAspSer

PheLeuLeuTyrMetCysLeuGluThrGlyAlaIleSerPheValGlnLeuPheAspProGlyPheGluValGlnValGlyLysArgSer

ThrGluAlaArgHisGlyValArgIleAspThrSerHisArgSerLeuIleLeuLysCysSerSerTyrArgGlnAlaArgTrpTrpAla

GlnGluIleThrGluLeuAlaGlnGlyProGlyArgAspPheLeuGlnLeuHisArgHMetisAspSerTyrAlaProProArgProGly ThrLeuAlaArgTrpPheValAsnGlyAlaGlyTyrPheAlaAlaValAlaAspAlaIleLeuArgAlaGlnGluGluIlePheIleThr AspTrpTrpLeuSerProGluValTyrLeuLysArgProAlaHisSerAspAspTrpArgLeuAspIleMetPheLysArgLysAlaGlu GluGlyValArgValSerIleLeuLeuPheLysGluLeuGluLeuAlaLeuGlyIleAsnSerGlyTyrSerLysArgAlaLeuMetLeu LeuHisProAsnIleLysValMetArgHisProAspGlnValThrLeuTrpAlaHisHisGluLysLeuLeuValValAspGlnValVal AlaPheLeuGlyGlyLeuAspLeuAlaTyrGlyArgTrpAspAspLeuHisTyrArgLeuThrAspLeuGlyAspSerSerGluSerAla AlaSerGlnProProThrProArgProAspSerProAlaThrProAspLeuSerHisAsnGlnPhePheTrpLeuGlyLysAspTyrSer AsnLeuIleThrLysAspTrpValGlnLeuAspArgProPheGluAspPheIleAspArgGluThrThrProArgMetProTrpArgAsp ValGlyValValValHisGlyLeuProAlaArgAspLeuAlaArgHisPheIleGlnArgTrpAsnPheThrLysThrThrLysAlaLys TyrLysThrProThrTyrProTyrLeuLeuProLysSerThrSerThrAlaAsnGlnLeuProPheThrLeuProGlyGlyGlnCysThr ThrValGlnValLeuArgSerValAspArgTrpSerAlaGlyThrLeuGluAsnSerIleLeuAsnAlaTyrLeuHisThrIleArgGlu SerGlnHisPheLeuTyrIleGluAsnGlnPhePheIleSerCysSerAspGlyArgThrValLeuAsnLysValGlyAspGluIleVal AspArgIleLeuLysAlaHisLysGlnGlyTrpCysTyrArgValTyrValLeuLeuProLeuLeuProGlyPheGluGlyAspIleSer ThrGlyGlyGlyAsnSerIleGlnAlaIleLeuHisPheThrTyrArgThrLeuCysArgGlyGluTyrSerIleLeuHisArgLeuLys AlaAlaMetGlyThrAlaTrpArgAspTyrIleSerIleCysGlyLeuArgThrHisGlyGluLeuGlyGlyHisProValSerGluLeu IleTyrIleHisSerLysValLeuIleAlaAspAspArgThrValIleIleGlySerAlaAsnIleAsnAspArgSerLeuLeuGlyLys ArgAspSerGluLeuAlaValLeuIleGluAspThrGluThrGluProSerLeuMetAsnGlyAlaGluTyrGlnAlaGlyArgPheAla LeuSerLeuArgLysHisCysPheGlyValIleLeuGlyAlaAsnThrArgProAspLeuAspLeuArgAspProIleCysAspAspPhe PheGlnLeuTrpGlnAspMetAlaGluSerAsnAlaAsnIleTyrGluGlnIlePheArgCysLeuProSerAsnAlaThrArgSerLeu ArgThrLeuArgGluTyrValAlaValGluProLeuAlaThrValSerProProLeuAlaArgSerGluLeuThrGlnValGlnGlyHis LeuValHisPheProLeuLysPheLeuGluAspGluSerLeuLeuProProLeuGlySerLysGluGlyMetIleProLeuGluValTrp ThrSTP
```

Recombinant Production of PLD2

A further aspect of the present invention is a method for producing a PLD2 protein comprising:
 a) obtaining a DNA sequence according to claim 1 encoding a PLD2 protein;
 b) inserting said DNA into a host cell and expressing said PLD2 protein; and
 c) isolating said PLD2 protein.

Preferably, the PD2 protein has an amino acid sequence at least 90% sequence identical to SEQ ID NO. 2, more preferably an amino acid sequence at least 95% sequence identical to SEQ ID NO. 2, and most preferably an amino acid sequence at least 98% sequence identical to SEQ ID NO. 2. Even more preferably, the PLD2 protein has biological activity, particularly functional characteristics such as, for example, activity in a PLD assay.

The nucleotide sequence of the present invention can be expressed in a suitable host cell to produce active PLD2 protein. Expression occurs by placing a nucleotide sequence of the invention into an appropriate expression vector and introducing the expression vector into a suitable host cell, growing the transformed host cell, inducing the expression of PLD2, and purifying the recombinant PLD2 from the host cell to obtain purified, and preferably active, PLD2. Appropriate expression vectors are known in the art. For example, pET-14b, pCDNA1Amp, and pVL1392 are available from Novagen and Invitrogen and are suitable vectors for expression in *E. coli*, COS cells and baculovirus infected insect cells, respectively. These vectors are illustrative of those that are known in the art. Suitable host cells can be any cell capable of growth in a suitable media and allowing purification of the expressed PLD2. Examples of suitable host cells include *E. coli* (e.g., strain DHIQ, Gibco-BRL (Gaithersburg, Md.), or strain BL21 (DE3), Novagen, (Madison, Wis.), baculovirus infected cell cultures (such as insect cell cultures including SF9 cells), yeast (such as Pichia) and mammalian cells (such as COS monkey cells as described in for example Sambrook et al., *Molecular Cloning, A Laboratory Manual*, 2nd Edition (1989), Cold Spring Harbor Press, Cold Spring Harbor, N.Y. Expression in *E. coli* often results in expression of the PLD2 in inclusion bodies which may require a modification in the purification procedure. Another possible alternative is to express the PLD2 at the organism level, for example in plants or higher animals. Baculovirus infection of insect larvae and harvesting of the insect larvae for expressed proteins ("caterpillar harvest") has also been achieved for various proteins to produce active protein (e.g., Luckow, (1993) Curr. Opin. Biotechnol. 4:564–572; Pajot-Augy et al., (1995) J. Mol. Endocrinol. 14:51–66). The preferred expression system for the present invention is baculovirus infected insect cell cultures.

Growth of the transformed host cells can occur under conditions that are known in the art. The conditions will generally depend upon the host cell and the type of vector used. Suitable induction conditions may be used such as temperature and chemicals and will depend on the type of promoter utilized. When baculovirus infected insect cells are used, preferred conditions for fermentation include using Grace's insect media (Luckow and Summers (1988) Virology 170:31–39) at about room temperature.

Purification of the PLD2 can be accomplished using known techniques without performing undue experimentation. Generally, the transformed cells expressing the PLD2 are broken, crude purification occurs to remove debris and some contaminating proteins, followed by chromatography to further purify the PLD2 to the desired level of purity. Cells can be broken by known techniques such as homongenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatogaphy (HPLC), gel filtration, affinity chromatography, hydrophobic interaction chromatography, etc. PLS is in monomeric form according to all available data. A preferred purification method for baculovirus infected insect cells can include sonication, ammonium sulfate precipitation (40–70% cut), hydrophobic interaction column (preferably phenyl sepharose), followed by anion exchange chromatography (preferably mono-Q sepharose). DTT is preferably used during the anion exchange chromatography.

Therefore, the nucleotide sequences of the present invention preferably result in the production of active PLD2 when expressed in a suitable host cell and purified.

The PLD2 protein preferably has biological activity. Biological activity can refer to structural or functional characteristics of the protein that result in characteristic interactions with other molecules. Biological activity can include structural characteristics such as one or more of the following: immunological reactivity, three dimensional conformation as indicated by spectrophotometry (infra red, U.V.- Visible, NMR, X-ray, etc.) similar amino acid sequence, Michaelis-Menton constants (Km), weight of the holoenzyme, terminal nucleotide sequence corresponding to an appropriate terminal amino acid sequence, pl, and inhibition constants (Ki) of various inhibitors. Biological activity can also include functional characteristics such as enzymatic activity of the protein in vitro or in vivo. For example, PLD assays have been described in the literature (e.g., Steed et al. (1996) Biochemistry 35:5229–5237; Colley et al., (1997) Current Biology 7: 191–201) and herein (e.g., EXAMPLE 7). Another functional characteristic is the ability of a protein or polypeptide to be recognized by antibodies which have been generated against a protein having an amino acid sequence of PLD2 as described above.

Antibodies to PLD2

Antibodies that specifically recognize epitopes within the amino acid sequence of SEQ ID NO. 2 are also encompassed by this invention. Antibodies to PLD2 can be obtained in a variety of ways. The isolated PLD2 can be used as an immunogen to raise antibodies in a test animal. If the antibodies are raised in mice, monoclonal antibodies can be prepared using known techniques. Moreover, chimeric antibodies and humanized antibodies, single chain antibodies, Fab fragments, F(ab')2 fragments, and epitope-binding fragments of any of the above can also be made by those of skill in the art. Otherwise, the polyclonal antibodies raised in the animals can be used. Also, instead of using the full length PLD2 as the immunogen, shorter segments of the PLD2 can be used as can synthetic peptides having a sequence corresponding to a portion of the PLD2, preferably a portion containing the epitope for antigenicity and solicitation of antibodies. Preferred peptides are a PLD2 protein comprising a protein having an amino acid sequence that is at least about 90% sequence identical to SEQ ID NO. 2. Preferably, the isolated protein has an amino acid sequence that is at least 95% sequence identical to SEQ ID NO. 2, more preferably at least 98% sequence identical to SEQ ID NO. 2. The antibodies against PLD2 are therefore useful as a measure of biological activity and in the detection of PLD2 in a biological sample, and may therefore be used as part of a diagnostic or prognostic technique whereby patients are tested for abnormal amounts of PLD2, e.g., an assay to measure the level of PLD2 protein in a biological sample. They can also be useful as modulators of PLD2 activity in a mammal. Administration of such antibodies could lead to recognition and inactivation of PLD2 in a mammal, especially when the inactivation of PLD2 in a mammal could have medical and therapeutic benefits.

For the production of antibodies of the invention, a host animal is immunized by injection with a peptide containing the amino acid sequence of SEQ. ID NO: 2. Such host animals may include but are not limited to rabbits, mice, and rats, to name but a few. Various adjuvants may be used to increase the immunological response, depending on the host species, including but not limited to Freund's (complete and incomplete) adjuvant, mineral gels such as aluminum hydroxide, lysolecithin, pluronic polyols, polyanions, peptides, oil emulsions, BCG (bacille Calmette-Guerin) and *Corynebacterium parvum*. Polyclonal antibodies are heterogeneous populations of antibody molecules derived from the sera of the immunized animals.

In order to further enhance immunogenicity, the immunogen may be coupled to a carrier. Examples of such carriers are keyhole limpet hemocyanin (KLH) and bovine serum albumin (BSA). Other albumins such as ovalbumin, mouse serum albumin or rabbit serum albumin can also be used as carriers. Methods of coupling a peptide to a carrier are well known in the art and include the use of glutaraldehyde, carbodiimide and m-maleimidobenzoyl-N-hydroxysuccinimide ester.

Since epitopes within SEQ ID NO: 2 are predicted to interact with the substrates of PLD2, they would be exposed on the surface of PLD2. Therefore, they would not be predicted to be "hidden" epitopes when immunizing with intact PLD2. The amount of antigen to be used can be determined readily by those which average skill in the art without undue experimentation. The antigen can be administered by a number of routes (subcutaneous, intramuscular, intradermal, intravenous and intraperitoneal). The production of polyclonal antibodies is monitored by sampling blood of the immunized animal at various time points after administration. When the desired level of antibody is obtained, the animal is bled and the serum is stored.

Monoclonal antibodies (mAb), which are homogenous populations of antibodies to a particular antigen, may be obtained by any technique which provides for the production of antibody molecules by continuous cell lines in culture. These include, but are not limited to, the hybridoma technique [Kohler and Milstein (1975) Nature 256:495–497; U.S. Pat. No. 4,376,110; Howell and Lane (1988) Antibodies, A Laboratory Manual, Cold Spring Harbor Press, N.Y.], the human B-cell hybridoma technique [Kosbor et al. (1983) Immunology Today 4:72; Cole et al. (1983) Proc. Natl. Acad. Sci U.S.A. 80:2026], and the EBV-hybridoma technique [Cole et al. (1985), Monoclonal Antibodies And Cancer Therapy, Alan R. Liss, Inc.]. Such antibodies may be of any immunoglobulin class including IgG, IgM, IgE, IgA, IgD and any subclass thereof.

In addition, techniques developed for the production of "chimeric antibodies" can be used (Morrison et al. (1984) Proc. Natl. Acad. Sci. U.S.A. 81:6851; Neuberger et. al. (1984) Nature 312:604; Takeda et al. (1985) Nature 314:452). These involve splicing a portion of a gene encoding a mouse antibody of appropriate antigen specificity to a portion of a gene encoding a human antibody of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird (1988) Science 242:423; Huston et al. (1988) Proc. Natl. Acad. Sci. U.S.A. 85:5879; and Ward et al. (1989) Nature 334:544) can be adapted to product single chain antibodies against the epitopes of SEQ ID NO: 2. Single chain antibodies are formed by linking the heavy and light chain fragments of the $F_v$ region via an amino acid bridge, resulting in a single chain polypeptide. They are conveniently produced by recombinant DNA techniques.

Antibody fragments which recognize specific epitopes may be generated by known techniques. For example, such fragments include but are not limited to the $F(ab')_2$ fragments which can be produced by pepsin digestion of the antibody molecule, and the Fab fragments which can be generated by reducing the disulfide bridges of the $F(ab')_2$ fragments. Alternatively, Fab expression libraries may be constructed (Huse et al. (1989) Science 246:1275) to allow rapid and easy identification of monoclonal Fab fragments with the desired specificity.

Methods for screening antibodies for binding specificity are well known. These include but are not restricted to testing for: (a) binding to a peptide containing the amino acid sequence of SEQ ID NO: 2; (b) lack of binding to peptides and polypeptides lacking these sequences; and (c) inhibition of binding to intact PLD2 by peptides containing the amino acid sequence of SEQ ID NO: 2.

Measuring PLD2 Gene Activity and Measuring PLD2 Protein Levels

The present invention includes methods for the measurement of PLD2 gene activity and measurement of PLD2 protein levels in a mammal. The measurement of PLD2 gene activity in a mammal comprises:

a) obtaining a gene sample from the mammal;

b) combining the gene sample with a portion of the isolated polynucleotides according to the present invention under conditions of high stringency, wherein said portion is at least 8–20 nucleotides in length; and c) measuring the amount of hybridization between the gene sample and the isolated polynucleotide.

Conditions of high stringency include hybridization, under stringent hybridization conditions, of a nucleic acid sequence to a specified nucleic acid target sequence to a detectably greater degree that its hybridization to non-target nucleic acid sequences. Selectively hybridizing sequences have at least 90% sequence identity, preferably 95% sequence identity, and most preferably 98–100% sequence identity (i.e., complementarity) with each other. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Conditions of high stringency or stringent conditions in the context of nucleic acid hybridization assay formats are sequence dependent, and are different under different environmental parameters. An extensive guide to hybridization of nucleic acids is found in Tijssen (1993) *Laboratory Techniques in Biochemistry and Molecular Biology—Hybridization with Nucleic Acid Probes* Part 1, Chapter 2 "Overview of Principles of Hybridization and the Strategy of Nucleic Acid Probe Assays" Elsevier, New York. Generally, highly stringent conditions are selected to be about 5° C. lower than the thermal melting point $T_m$ for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular nucleic acid of the present invention. This occurs, e.g., when a copy of a nucleic acid is created using the maximum codon degeneracy permitted by the genetic code. Stringent hybridization conditions are sequence-dependent and will be different in different circumstances. Longer sequences hybridize specifically at higher temperatures.

The portion of the isolated polynucleotides according to the present invention that are used can vary. Usually, 8–25 nucleotides in length is necessary for hybridization of completely complementary oligonucleotides. The length of the portion can be longer, particularly if there are any mismatches and a longer portion with or without mismatches is desirable so that the fidelity of the hybridization (the $T_m$) is higher and less likely to occur between the portion of PLD2 oligonucleotide and a gene sample. Consequently, the preferred length of the portion of oligonucleotide is at least 8–20 nucleotides, more preferably at least 20–100 and most preferably at least 50% of the nucleotides from the coding region of PLD2 oligonucleotides according to the present invention.

The measurement of PLD2 protein levels in a mammal comprises:

1) obtaining a sample from a mammal;
2) incubating the sample with an anti-PLD2 antibody; and
3) measuring the level of bound anti-PLD2 antibody in the sample.

Preferably, the sample is obtained from a patient, especially a human patient, The sample can be a body fluid such as for example, urine, saliva, synovial fluid or serum. The sample may be obtained from a localized site such as a tumor or damaged tissue. The preferred anti-PLD2 antibody is produced in a rodent such as a rat, mouse or rabbit sensitized with a PLD2 protein having the amino acid sequence of SEQ ID NO: 2. Incubation of the sample with a PLD2 antibody takes place in any suitable buffer for sufficient time for antibody to bind to the PLD2. The conditions for incubation are known in the art and should be at a temperature to allow binding but without degradation of the protein or antibody. The preferred method of measuring the level of bound anti-PLD2 antibody is Western blotting following electrophoresis, although other methods of measuring bound antibodies are well known in the art once an antibody according to the present invention has been obtained.

The present invention also includes a kit for performing the assay aspect of the invention. Such a kit includes a solution or mixture of one or anti-PLD2 antibody. The kit may additionally contain vials or vessels for incubating a sample, viscosity reducer, a reducing agent inactivating substance and or separation materials.

Another aspect of the present invention is a method for modulating the level of PLD2 in a mammal comprising modulating the level of active PLD2 protein in a mammal wherein said modulation is selected from the group consisting of increasing or decreasing the level of active PLD2 protein in said mammal.

Increasing the level of active PLD2 protein in a mammal can be by administration of a therapeutically effective amount of PLD2 protein when the PLD2 protein is the active ingredient in a pharmaceutical formulation. Administration of a therapeutically effective amount of PLD2 can also be by gene therapy wherein the PLD2 gene is engineered into or added to some or all of the cells of a patient in having a PLD2 deficiency.

It is well known in the medical arts that dosages for any one patient depend on many factors, as well as the particular compound to be administered, the time and route of administration and other drugs being administered concurrently. Dosages for the peptides or proteins of the invention will vary, but can be, when administered intravenously approximately 0.01 mg to 10 mg/ml blood volume. Routes and doses of administration are well known to skilled pharmacologists and physicians. Routes, in additions to those described, include but are not restricted to: intraperitoneal, intramuscular, intrapulmonary, transmucosal, subcutaneous and intravenous.

A peptide or protein of the invention may be delivered to cells of a patient in its unmodified state, dissolved in an appropriate physiological solution, e.g. physiological saline. Alternatively, it may be modified as detailed above to facilitate transport across cell and/or intracellular membranes and to prevent extracellular or intracellular degradation. Its transport across biological membranes may also be enhanced by delivering it encapsulated in liposomes (Gabizon et al. (1990) Cancer Res. 50:6371; Ranade (1989) J. Clin. Pharmacol. 29:685) or an appropriate biodegradable polymeric microparticle (also referred to as a "microsphere", "nanosphere", "nanoparticle" or "microcapsule"). Naturally, it is desirable that these peptides and proteins be selectively targeted to relevant tissues and cell types. This can be achieved by contacting the proteins directly with the affected organ or tissue, e.g., by localized injection or implantation. Thus, in autoimmune diseases such as rheumatoid arthritis (RA) or insulin dependent diabetes mellitus (IDDM), the peptides and proteins could be introduced directly into the affected joints or the pancreas, respectively, or, preferably, into draining lymphoid tissue in which the active autoimmune response occurs. The latter procedure would obviate the potential tissue damage causes by introducing pro-apoptotic peptides and proteins into the cells of the target organ.

Alternatively, peptides and proteins of the invention may be delivered in liposomes into which have been incorporated ligands for receptors on relevant cells (e.g., T cells or B cells) or antibodies to cell-surface markers expressed by these cells. Thus an antibody specific for the CD4 T cell surface marker may direct to liposomes containing both the anti-CD4 antibody and the relevant pro-apoptotic peptide or protein to a CD4+ T cell. In autoimmune diseases in which the T cell receptor (TCR) expressed by a dominant pathogenic T-cell clone has been defined, an antibody specific for the relevant TCR component (e.g., Vβ) may be used. The latter methodology would represent an ideal form of immunotherapy in which pathogenic effector cells are specifically targeted for elimination while the immune system as a whole and the cells of the target organ remain uncompromised. The same approach of targeting T cells both CD4+ and CD8+, could be used in transplant recipients.

Delivery of the proteins of the invention can also occur through gene therapy wherein some or all of the cells of a patient are modified by the addition of genetic material capable of coding for PLD2 such that the modified cells produce the PLD2 protein in vivo. Modification of the cells most often occurs through the use of an expression vector. An expression vector is composed of or contains a nucleic acid in which a polynucleotide of the invention is operatively linked to a promoter or enhancer-promoter combination. A promoter is a transcriptional regulatory element composed of a region of DNA typically within 100 nucleotides pairs in front of (upstream of) the point at which transcription starts. Another transcriptional regulatory element is an enhancer, An enhancer provides specificity in terms of time, location and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region. To bring a coding sequence under control of a promoter, it is necessary to position the translation initiation site of the translational reading from of the peptide or protein between one and about fifty nucleotides downstream (3') of the promoter. Examples of particular promoters are known in the art, such as, for example, a-fetoprotein promoter for hepatocellular carcinoma (Huber et al. (1991) Proc. Nat. Acad. Sci. U.S.A. 88:8039); the DF# tumor antigen promoter enhancer for certain breast and lung carcinomas (Abe and Kufe (1993) Proc. Nat. Acad. Sci. U.S.A. 90:282) or the tyrosinase promoter for melanoma (Hart et al., (1995) Br. Med. Bull. 51:647). Additionally ribosome binding sites and signal peptides may also be included in the expression vector. Expression vectors and methods for their construction are known in the art.

Suitable vectors include plasmids and viral vectors such as herpes viruses, retroviruses, canary pox viruses, adenoviruses and adeno-associated viruses, among others. The vectors are then usually introduced into cells in vivo. The in vivo approach requires delivery of a genetic construct directly into the patient, preferably targeting it to the cells or tissue of interest. Consequently, it is often desirable for the promoter and other elements of the expression vector to be compatible with the cell being targeted.

For example, in cancer, after surgical removal of a primary tumor, residual cells may be targeted by treating the vicinity of the tumor with a composition containing a retroviral vector encoding PLD2. Alternatively, instead of surgery, the primary tumor could be treated by injection of the vector directly into the tumor. Malignant cells distal to the primary tumor site may be reached by delivering the vector intravenously. General methods for gene therapy and introduction of genes into somatic tissue and cells is known in the art (e.g., U.S. Pat. Nos. 5,648,241; 5,645,829; 5,631,236; and 5,399,346).

Decreasing the level of active PLD2 protein in a mammal can be by removal or inactivation of the PLD2 protein or by decreasing the expression of the PLD2 gene. For example, removal or inactivation of PLD2 protein can be achieved by administration of a therapeutically effective amount of an anti-PLD2 antibody or other ligand that will bind to PLD2 and prevent it from binding to its usual substrate. Decreasing the expression of the PLD2 gene can occur by, for example, administration of a therapeutically effective amount of an antisense oligonucleotide against PLD2, e.g., an oligonucleotide that hybridizes to all or a part of the PLD2 gene or RNA.

The antibodies of the invention specific for PLD2 can be administered using the methods and techniques similar to those used for administration of the PLD2 protein.

For antisense treatment, oligonucleotides may be administered in a pharmaceutical acceptable carrier, Pharmaceutical acceptable carriers are biologically compatible vehicles which are suitable for administration to a human, e.g., physiological saline. A therapeutically effective amount of an oligonucleotide is an amount of oligonucleotide of the invention which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of oligonucleotide is from approximately $10^6$ to $10^{12}$ copies of the oligonucleotide molecule. This dose can be repeatedly administered, as needed. Routes of administration will be as for the peptides described.

The oligonucleotide will preferably have all or a portion of the base sequence in SEQ ID NO: 1 or have a base sequence that is complementary to all or a portion of the base sequence in SEQ ID NO: 1. For effective use as an antisense molecule, an oligonucleotide needs to exhibit specificity, fidelity and stability. Therefor, the length of the portion of the oligonucleotide should be long enough so that the sequence will hybridize selectively (i.e., with specificity) with PLD2 coding DNA or RNA with minimal or no cross hybridization with other genes or RNA coding for other proteins. Therefore, the length of the portion will depend on the region of SEQ ID NO: 1 that is targeted. The desired or optimal length of the antisense oligonucleotide will also be influenced by the desire for fidelity of binding of the oligonucleotide to the target. Generally, longer oligonucleotides have more fidelity since there are more base pairs that can match. As a result, the antisense molecules of the present invention are at least 8–20 nucleotides, more preferably at least 20–100 and most preferably at least 50% of the nucleotides from the coding region of PLD2 oligonucleotides according to the present invention. To promote stability of the antisense molecule, the phosphate or sugar components of the oligonucleotide may be modified to make the oligonucleotide less susceptible to nucleases and other degradation. Numerous modifications are known in the art as described for example in U.S. Pat. Nos. 5,644,048; 5,637,684; 5,635,488; 5,623,070; 5,623,065; 5,618,704; 5,614,617; 5,610,058; 5,602,240 and references cited therein.

The pharmaceutical compositions according to the invention are those for enteral (including oral or rectal) and parenteral (including intravenous, transdermal or intraarterial biodegradable stent) administration to a mammal, i.e. a warm-blooded animal or human. The daily dose of the active ingredients depends on the age and the individual condition and also on the manner of administration.

The pharmaceutical compositions contain, for example, from about 10% to about 80%, preferably from about 20% to about 60%, of the active ingredient. Pharmaceutical compositions according to the invention for enteral or parenteral administration are, for example, those in unit dose forms, such as sugar-coated tablets, tablets, capsules, gel caps, caplets, or suppositories, and furthermore ampoules. The compositions may also be in sublingual dosages, sustained release formulations and elixirs. These are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example, to identify or to indicate different doses of active ingredient, may be added to the tablets or sugar-coated tablet coatings.

Other orally utilizable pharmaceutical preparations are hard gelatin capsules, and also soft closed capsules made of gelatin and a plasticizer, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, paraffin oil or liquid polyethylene glycols, it also being possible to add stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

When necessary or desirable, the active agent can be formulated with standard excipients and appropriate coating materials to obtain immediate release, controlled release or sustained release dosage forms. Such excipients include, but are not limited to: titanium dioxide, talc; starch; microcrystalline cellulose, microgranular cellulose, casein formaldehyde, colloidal silicon dioxide; lubricants such as magnesium stearate; colorants such as iron oxide; Eudragit coating materials, polyvinyl pyrrolidone, polyethyleneglycols, alumina, carboxymethylcellulose, and gelatin. Alternative specific formulations are disclosed in U.S. Pat. No. 3,859,437; and U.S. Pat. No. 4,263,272. Still other formulations will be readily apparent to those of ordinary skill in the pharmaceutical formulation art.

While any mammal may be treated with the present invention, the invention is primarily directed toward humans, farm animals, and pets; most preferably humans.

For purposes of the present invention, the at risk population of one or more of the mammals to be treated includes those having been diagnosed with PLD-dependent diseases.

The present invention includes methods of treatment for PLD dependent diseases and conditions, particularly PLD2 dependent diseases and conditions. Diagnosis of PLD dependent diseases would be able to be performed by a medical practitioner who is skilled in the art of treatment of proliferative type diseases. Illustratively, PLD dependent diseases that can be diagnosed by a skilled clinician or physician and which are treatable by the present invention include cancer, proliferation of tumours, particularly those tumours that result from an activated oncogene involving angiogenesis stimulated by production of fibroblast growth factor (FGF), vascular endothelial growth factor (VEGF), or platelet derived growth factor (PDGF), tumor invasion and formation of metastases through adhesion molecule binding, expressed by vascular endothelial cells (VCAM and ICAM), tissue invasion through protease production such as MMP-9; autoimmune diseases such as those caused by disregulation of the T cell or B cell immune systems, treatable by suppression of the T cell or B cell responses; acute allergic reactions illustratively including asthma and chronic inflammatory diseases, mediated by proinflammatory cytokines including tumor necrosis factor (TNF) and IL-1; rheumatoid arthritis, osteoarthritis, multiple sclerosis, or insulin dependent diabetes mellitus, particularly those that are associated with enhanced localization of inflammatory cells and release of inflammatory cytokines and metalloproteases; decreased hematopoesis; antigen activation of T cells; antigen activated antibody secretion by B cells; activation of macrophage or endothelial cells by endotoxins, Tumor Necrosis Factor (TNF), interleukin-1 (IL-1) or granulocyte macrophage colony stimulating factor (GM-CSF); decreased resistance of mesenchymal cells to TNF; proliferation of smooth muscle cells, endothelial cells, fibroblasts, and other cell types in response to growth factors, such as PDGF, FGF, epidermal growth factor (EGF), and the like (i.e. associated with atherosclerosis, restenosis, stroke, and coronary artery disease); activation of human immunodeficiency virus infection and the associated HIV-dementia and T-cell activation; proliferation of kidney mesangial cells in response to IL-1 and microtubule activating protein-1a (mip-1a); kidney glomerular toxicity in response to cyclosporin A or amphotericin B treatment; suppression of Steel Factor (also called stem cell factor and mast cell growth factor), Granulocyte Colony Stimulating Factor (G-CSF), oncostatin M, or interleukin 6 (IL-6) in bone marrow stromal cells in response to TNF; the expression of adhesion molecules in endothelial cells and adhesion of inflammation cells to endothelial cells; cytotoxicity of gastrointestinal or pulmonary epithelial cells in response to a cytotoxic drug or radiation; inflammatory stimuli-induced production of metalloproteases in synovial cells, fibroblasts, and glomerular epithelial cells; bone diseases caused by IL-1 stimulated overproduction of osteoclast-activating factor by osteoclasts; immunoglobulin E (IgE) or RANTES stimulated degranulation of mast cells and basophils; improper modulation of the signal transduction of epinephrine and acetylcholine in the neural pathways in which they are utilized; activation of platelet activating factor in inflammation cells; the release of the pro-inflammatory cytokines TNF, IL-1, IL-2, and Granulocyte Macrophage Colony Stimulating Factor (GM-CSF) in various cell types in response to inflammatory stimuli; activation and proliferation of lymphocytes and other cell types in response to IL-1 and IL-2, and the like, including the clinical manifestations of these cellular events.

All references cited in this specification are hereby incorporated by reference. The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

EXAMPLES

The examples are provided to describe specific embodiments of the invention and are not to be construed as limiting the invention in any way.

Example 1

Cloning cDNA's Representing the 3' Region of Human PLD2

Via EST-Derived rtPCR

Using the mouse sequence of PLD2 reported by Colley et al. ((1997) Current Biology 7, 191–201; GenBank Accession #U87557), 7 human EST's from the Genbank database were found to represent parts of the human PLD2, covering approximately one fourth of the gene at the 3' end of the coding region and 3' untranslated region albeit with unreliable and partially incorrect sequence data (Accession numbers: W75418, W61990, W66743, R93485, R83570, H02092, R69739, H01995, R93432, R97756). The PCR reactions were performed on an MJ Research PCT-200 thermal cycler (Watertown, Mass.) with a 3-step amplification at an annealing temperature of 62° C. (using Advantage high-fidelity PCR polymerase (Clontech Laboratories, Palo Alto, Calif.). The template was human brain Marathon-Ready cDNA (Clontech). The entire 50 mM reaction was separated by electrophoresis in a 0.8% SeaPlaque low gelling temperature agarose TBE gel (FMC Bioproducts, Rockland, Me.) and the approximately 1.0 kB PCR product isolated by dissection. The DNA's were purified from the gel slice with a Wizard PCR prep DNA purification system (Promega, Madison, Wis.) and cloned via the pCR2.1 TOPO kit from Invitrogen Corp. (Carlsbad, Calif.) and the primers used were: 5'-TACAGGACCCTGTGTCGTGGG-3' (SEQ ID NO. 3) AND 5'-CTCCACCTTGGCAGCAATGG-3' (SEQ ID NO. 4). Potential clones were isolated and screened for inserted cDNA fragments using standard methods.

Example 2

DNA Sequence Analysis of Human PLD2

Two independent clones of the 3' end of human PLD2 were sequenced with primers annealing to the ends of the insertion site in the pCR2.1 cloning vector. Using this sequence, oligonucleotides were designed and utilized to obtain the sequence of both strands for both clones. Few discrepancies were found and in these cases, at least two of the EST's provided the information required for base calling. DNA for sequencing was prepared with a Wizard 343 purification kit (Promega), reactions were performed with AmpliTaq DNA polymerase, FS (Perkin Elmer Corp, Foster City, Calif.) and data obtained on an ABI 277 automated sequencer (Perkin Elmer).

Example 3

Cloning the Bulk of Human PLD2 by 5' RACE

Using the sequence obtained from the hPLD2 3' clones in EXAMPLE 2, an oligonucleotide primer was designed for 5' RACE (rapid amplification of cDNA ends; sequence: 5'CCGTGTGTACGAAGCCCGCAGATGG3') (SEQ ID NO. 5). Human brain Marathon-Ready cDNA (Clontech) was used as a template with the PLD2-specific primer and the AP-1 provided with the template. The a "Touchdown" PCR reaction provided a single identifiable fragment of approximately 2.7 kB on Agarose electrophoresis. This fragment was isolated, cloned and sequenced as described above. Since there is no EST information available for this region of the cDNA, 5 independent clones were analyzed to obtain reliable sequence information.

The human phospholipase D2 cDNA sequence that was obtained was 3388 base pairs long as follows (SEQ ID NO. 1).

```
CCATCCTAAT ACGACTCACT ATAGGGCTCG AGCGGCCGCC CGGGCAGGTC CGGCCCCGCT  60    SEQ ID NO. 1

TCGGCCGGCC CCGCCTCGGC CGGGGCGTGG GCTCCGGCTG CAGCTCCGGT CTGCTCTCTT  120

GGCTCGGGAA CCCCCGCGGG CGCTGGCTCC GTCTGCCAGG GATGACGGCG ACCCCTGAGA  180

GCCTCTTCCC CACTGGGGAC GAACTGGACT CCAGCCAGCT CCAGATGGAG TCCGATGAGG  240

TGGACACCCT GAAGGAGGGA GAGGACCCAG CCGACCGGAT GCACCCGTTT CTGGCCATCT  300

ATGAGCTTCA GTCTCTGAAA GTGCACCCCT TGGTGTTCGC ACCTGGGGTC CCTGTCACAG  360

CCCAGGTGGT GGGCACCGAA AGATATACCA GCGGATCCAA GGTGGGAACC TGCACTCTGT  420

ATTCTGTCCG CTTGACTCAC GGCGACTTTT CCTGGACAAC CAAGAAGAAA TACCGTCATT  480

TTCAGGAGCT GCATCGGGAC CTCCTGAGAC ACAAAGTCTT GATGAGTCTG CTCCCTCTGG  540

CTCGATTTGC CGTTGCCTAT TCTCCAGCCC GAGATGCAGG CAACAGAAAG ATGCCCTCTC  600

TACCCCGGGC AGGTCCTGAG GGCTCCACCA GACATGCAGC CAGCAAACAG AAATACCTGG  660

AGAATTACCT CAACCGTCTC TTGACCATGT CTTTCTATCG CAACTACCAT GCCATGACAG  720

AGTTCCTGGA AGTCAGTCAG CTGTCCTTTA TCCCGGACTT GGGCCGCAAA GGACTGGAGG  780

GGATGATCCG GAAGCGCTCA GGTGGCCACC GTGTTCCTGG CCTCACCTGC TGTGGCCGAG  840
```

-continued

```
ACCAAGTTTG TTATCGCTGG TCCAAGAAGT GGCTGGTGGT GAAGGACTCC TTCCTGCTGT    900
ACATGTGCCT CGAGACAGGT GCCATCTCAT TTGTTCAGCT CTTTGACCCT GGCTTTGAAG    960
TGCAAGTGGG GAAAAGGAGC ACGGAAGCAC GGCACGGCGT GCGGATCGAT ACCTCCCACA   1020
GGTCCTTGAT TCTCAAGTGC AGCAGCTACC GGCAGGCACG GTGGTGGGCC CAAGAAATCA   1080
CTGAGCTGGC ACAGGGCCCA GGCAGAAACT TCCTACAGCT GCACCGGCAT GACAGCTACG   1140
CCCCACCCCG GCCTGGGAAC TTGGCCCGGT GGTTTGTGAA TGGGGCAAGT TACTTTGCTG   1200
CTGTGGCAGA TGCCATCCTT CGAGCTCAAG AGGAGATTTT CATCACAGAC TGGTGGTTGA   1260
GTCCTGAGGT TTACCTGAAG CGTCCGGCCC ATTCAGATGA CTGGAGACTG GACATTATGT   1320
TCAAGAGGAA GGCGGAGGAA GGTGTCCGTG TGTCTATTCT GCTGTTTAAA GAAGTGGAAT   1380
TGGCCTTGGG CATCAACAGT GGCTATAGCA AGAGGGCGCT GATGCTGCTG CACCCCAACA   1440
TAAAGGTGAT GCGTCACCCA GACCAAGTGA CGTTGTGGGC CCATCATGAG AAGCTCCTGG   1500
TGGTGGACCA AGTGGTAGCA TTCCTGGGGG ACTGGACCT TGCCTATGGC CGCTGGGATG   1560
ACCTGCACTA CCGACTGACT GACCTTGGAG ACTCTTCTGA ATCAGCTGCT TCCCAGCTTC   1620
CCACCCCGCG CCCAGACTCA CCAGCCACCC CAGACTTCTT TCACAACCAA TTCTTCTGGC   1680
TGGGCAAGGA CTACAGCAAT CTTATCACCA AGGACTGGGT GCAGCTGGAC CGGCCTTTCG   1740
AAGATTTCAT TGACAGGGAG ACGACCCCTC GGATGCCATG GCGGGACGTT GGGGTGGTCG   1800
TCCATGGCCT ACCGGCCCGG GACCTTGCCC GGCACTTCAT CCAGCGCTGG AATTTCACCA   1860
AGACCACCAG GGCCAAGTAC AAGATTCCCA CATACCCCTA CCTGCTTCCC AAGTTTACCA   1920
GCACGGCCAA TCAGTTCCCC TTCACACTTC CAGGAGGGCA GTGCACCACC GTACAGGTCT   1980
TGCGATCAGT GGACCGCTGG TCAGCAGGGA CTCTGGAGAA CTCCATCCTC AATGCCTACC   2040
TGCACACCAT CAGGGAGAGC CAGCACTTCC TCTACATTGA GAATCAGTTC TTCATTAGCT   2100
GCTCAGATGG GCGGACGGTT CTGAACAAGG TGGGCGATGA GATTGTGGAC AGAATCCTGA   2160
AGGCCCACAA ACAGGGGTGG TGTTACCGAG TCTACGTGCT TTTGCCCTTA CTCCCTGGCT   2220
TCGAGGGTGA CATCTCCACG GGCGGTGGCA ACTCCATCCA GGCCATTCTG CACTTTACTT   2280
ACAGGACCCT GTGTCGTGGG GAGTATTCAA TCCTGCATCG CCTTAAAGCA GCCATGGGA   2340
CAGCATGGCG GGACTATATT TCCATCTGCG GGCTTCGTAC ACACGGAGAG CTGGGCGGGC   2400
ACCCCGTCTC GGAGCTCATC TACATCCACA GCAAGGTGCT CATCGCAGAT GACCGGACAG   2460
TCATCATTGG TTCTGCAAAC ATCAATGACC GGAGCTTGCT GGGGAAGCGG GACAGTGAGC   2520
TGGCCGTGCT GATCGAGGAC ACAGAGACGG AACCATCCCT CATGAATGGG GCAGAGTATC   2580
AGGCGGGCAG GTTTGCCTTG AGTCTGCGGA AGCACTGCTT CGGTGTGATT CTTGGAGCAA   2640
ATACCCGGCC AGACTTGGAT CTCCGAGACC CCATCTGTGA TGACTTCTTC CAGTTGTGGC   2700
AAGACATGGC TGAGAGCAAC GCCAATATCT ATGAGCAGAT CTTCCGCTGC CTGCCATCCA   2760
ATGCCACGCG TTCCCTGCGG ACTCTCCGGG AGTACGTGGC CGTGGAGCCC TTGGCCACGG   2820
TCAGTCCCCC CTTGGCTCGG TCTGAGCTCA CCCAGGTCCA GGGCCACCTG GTCCACTTCC   2880
CCCTCAAGTT CCTAGAGGAT GAGTCTTTGC TGCCCCCGCT GGGTAGCAAG GAGGGCATGA   2940
TCCCCCTAGA AGTGTGGACA TAGTTGAGGC CCCCGTCAGG GAGAGGTCAC CAGCTGCTGT   3000
GCCCCACCAC GTCTGGCTCC CTGCCCCTTA ACCCCAAGGA CTGAGGGCAG TGCCCTTTGA   3060
GATCTGGGGA GGCAGGCATT CCTGAAGGGA ACTAGAGGTG TTACAGAGGA CCCTTACGTG   3120
AGAAATAGCT GAAAAGGGCA CTCCCAACCC TGGGCTGGGG AGGAGGAGAG AGTCCCAGAG   3180
CTCATCCCCC CTGCTGCCCA GTGCAAACCA CTTCTCCATG CTGCAAAGGA GAAGCACAGC   3240
```

-continued
```
TCCTGCCAGG GTGAGCAGGG TCAAGCCTCT TATTCCAGGA GAAGGGCTC TGCCCCAGGC    3300

CCTACTACCC ATTGTTCCCT TCCTCTTCCT GCCCTTGAAC CCCCTCCCTG TCCCAGGGCC    3360

CTCCCAGCCC ATTGCTGCCA AGGTGGAG                                       3388
```

The coding region for the hPLD2 protein was coded for by the region 162–2963 of the cDNA sequence and is shown in SEQ ID NO. 2.

```
MetThrAlaThrProGluSerLeuPheProThrGlyAspGluLeuAspSerSerGlnLeuGlnMetGluSerAsp       SEQ ID NO. 2

GluValAspThrLeuLysGluGlyGluAspProAlaAspArgMetHisProPheLeuAlaIleTyrGluLeuGln

SerLeuLysValHisProLeuValPheAlaProGlyValProValThrAlaGlnValValGlyThrGluArgTyr

ThrSerGlySerLysValGlyThrCysThrLeuTyrSerValArgLeuThrHisGlyAspPheSerTrpThrThr

LysLysLysTyrArgHisPheGlnGluLeuHisArgAspLeuLeuArgHisLysValLeuMetSerLeuLeuPro

LeuAlaArgPheAlaValAlaTyrSerProAlaArgAspAlaGlyAsnArgLysMetProSerLeuProArgAla

GlyProGluGlySerThrArgHisAlaAlaSerLysGlnLysTyrLeuGluAsnTyrLeuAsnGlyLeuLeuThr

MetSerPheTyrArgAsnTyrHisAlaMetThrGluPheLeuGluValSerGlnLeuSerPheIleProAspLeu

GlyArgLysGlyLeuGluGlyMetIleArgLysArgSerGlyGlyHisArgValProGlyLeuThrCysCysGly

ArgAspGlnValCysTyrArgTrpSerLysArgTrpLeuValValLysAspSerPheLeuLeuTyrMetCysLeu

GluThrGlyAlaIleSerPheValGlnLeuPheAspProGlyPheGluValGlnValGlyLysArgSerThrGlu

AlaArgHisGlyValArgIleAspThrSerHisArgSerLeuIleLeuLysCysSerSerTyrArgGlnAlaArg

TrpTrpAlaGlnGluIleThrGluLeuAlaGlnGlyProGlyArgAspPheLeuGlnLeuHisArgHisAspSer

TyrAlaProProArgProGlyThrLeuAlaArgTrpPheValAsnGlyAlaGlyTyrPheAlaAlaValAlaAsp

AlaIleLeuArgAlaGlnGluGluIlePheIleThrAspTrpTrpLeuSerProGluValTyrLeuLysArgPro

AlaHisSerAspAspTrpArgLeuAspIleMetPheLysArgLysAlaGluGluGlyValArgValSerIleLeu

LeuPheLysGluLeuGluLeuAlaLeuGlyIleAsnSerGlyTyrSerLysArgAlaLeuMetLeuLeuHisPro

AsnIleLysValMetArgHisProAspGlnValThrLeuTrpAlaHisHisGluLysLeuLeuValValAspGln

ValValAlaPheLeuGlyGlyLeuAspLeuAlaTyrGlyArgTrpAspAspLeuHisTyrArgLeuThrAspLeu

GlyAspSerSerGluSerAlaAlaSerGlnProProThrProArgProAspSerProAlaThrProAspLeuSer

HisAsnGlnPhePheTrpLeuGlyLysAspTyrSerAsnLeuIleThrLysAspTrpValGlnLeuAspArgPro

PheGluAspPheIleAspArgGluThrThrProArgMetProTrpArgAspValGlyValValValHisGlyLeu

ProAlaArgAspLeuAlaArgHisPheIleGlnArgTrpAsnPheThrLysThrThrLysAlaLysTyrLysThr

ProThrTyrProTyrLeuLeuProLysSerThrSerThrAlaAsnGlnLeuProPheThrLeuProGlyGlyGln

CysThrThrValGlnValLeuArgSerValAspArgTrpSerAlaGlyThrLeuGluAsnSerIleLeuAsnAla

TyrLeuHisThrIleArgGluSerGlnHisPheLeuTyrIleGluAsnGlnPhePheIleSerCysSerAspGly

ArgThrValLeuAsnLysValGlyAspGluIleValAspArgIleLeuLysAlaHisLysGlnGlyTrpCysTyr

ArgValTyrValLeuLeuProLeuLeuProGlyPheGluGlyAspIleSerThrGlyGlyGlyAsnSerIleGln

AlaIleLeuHisPheThrTyrArgThrLeuCysArgGlyGluTyrSerIleLeuHisArgLeuLysAlaAlaMet

GlyThrAlaTrpArgAspTyrIleSerIleCysGlyLeuArgThrHisGlyGluLeuGlyGlyHisProValSer

GluLeuIleTyrIleHisSerLysValLeuIleAlaAspAspArgThrValIleIleGlySerAlaAsnIleAsn

AspArgSerLeuLeuGlyLysArgAspSerGluLeuAlaValLeuIleGluAspThrGluThrGluProSerLeu

MetAsnGlyAlaGluTyrGlnAlaGlyArgPheAlaLeuSerLeuArgLysHisCysPheGlyValIleLeuGly

AlaAsnThrArgProAspLeuAspLeuArgAspProIleCysAspAspPhePheGlnLeuTrpGlnAspMetAla
```

-continued

GluSerAsnAlaAsnIleTyrGluGlnIlePheArgCysLeuProSerAsnAlaThrArgSerLeuArgThrLeu

ArgGluTyrValAlaValGluProLeuAlaThrValSerProProLeuAlaArgSerGluLeuThrGlnValGln

GlyHisLeuValHisPheProLeuLysPheLeuGluAspGluSerLeuLeuProProLeuGlySerLysGluGly

MetIleProLeuGluValTrpThrSTP

Two splice variants hPLD2b and hPLD2c were also found as shown in SEQ ID NO. 6 and SEQ ID NO. 7, respectively. The splice variant hPLD2b deletes the bases 2588–2622 of SEQ ID NO. 1, while hPLD2c inserts the nucleotides GAGCTTTCTGGCTTCTGACTCCCCTGACCTCCTTGGCTTGGCCTCCCCCCA (SEQ ID NO. 8) after base 1170 in SEQ ID NO. 1, which causes early translational termination at base 1 172.

```
Protein Sequence for hPLD2b                                                    (SEQ ID NO. 6)
MetThrAlaThrProGluSerLeuPheProThrGlyAspGluLeuAspSerSerGlnLeuGlnMetGluSerAsp GluValAspThrLeuLysGluGlyGluAspProAlaAspArgMetHisProPheLeuAlaIleTyrGluLeuGln SerLeuLysValHisProLeuValPheAlaProGlyValProValThrAlaGlnValValGlyThrGluArgTyr ThrSerGlySerLysValGlyThrCysThrLeuTyrSerValArgLeuThrHisGlyAspPheSerTrpThrThr LysLysLysTyrArgHisPheGlnGluLeuHisArgAspLeuLeuArgHisLysValLeuMetSerLeuLeuPro LeuAlaArgPheAlaValAlaTyrSerProAlaArgAspAlaGlyAsnArgLysMetProSerLeuProArgAla GlyProGluGlySerThrArgHisAlaAlaSerLysGlnLysTyrLeuGluAsnTyrLeuAsnGlyLeuLeuThr MetSerPheTyrArgAsnTyrHisAlaMetThrGluPheLeuGluValSerGlnLeuSerPheIleProAspLeu GlyArgLysGlyLeuGluGlyMetIleArgLysArgSerGlyGlyHisArgValProGlyLeuThrCysCysGly ArgAspGlnValCysTyrArgTrpSerLysArgTrpLeuValValLysAspSerPheLeuLeuTyrMetCysLeu GluThrGlyAlaIleSerPheValGlnLeuPheAspProGlyPheGluValGlnValGlyLysArgSerThrGlu AlaArgHisGlyValArgIleAspThrSerHisArgSerLeuIleLeuLysCysSerSerTyrArgGlnAlaArg TrpTrpAlaGlnGluIleThrGluLeuAlaGlnGlyProGlyArgAspPheLeuGlnLeuHisArgHisAspSer TyrAlaProProArgProGlyThrLeuAlaArgTrpPheValAsnGlyAlaGlyTyrPheAlaAlaValAlaAsp AlaIleLeuArgAlaGlnGluGluIlePheIleThrAspTrpTrpLeuSerProGluValTyrLeuLysArgPro AlaHisSerAspAspTrpArgLeuAspIleMetPheLysArgLysAlaGluGluGlyValArgValSerIleLeu LeuPheLysGluLeuGluLeuAlaLeuGlyIleAsnSerGlyTyrSerLysArgAlaLeuMetLeuLeuHisPro AsnIleLysValMetArgHisProAspGlnValThrLeuTrpAlaHisHisGluLysLeuLeuValValAspGln ValValAlaPheLeuGlyGlyLeuAspLeuAlaTyrGlyArgTrpAspAspLeuHisTyrArgLeuThrAspLeu GlyAspSerSerGluSerAlaAlaSerGlnProProThrProArgProAspSerProAlaThrProAspLeuSer HisAsnGlnPhePheTrpLeuGlyLysAspTyrSerAsnLeuIleThrLysAspTrpValGlnLeuAspArgPro PheGluAspPheIleAspArgGluThrThrProArgMetProTrpArgAspValGlyValValValHisGlyLeu ProAlaArgAspLeuAlaArgHisPheIleGlnArgTrpAsnPheThrLysThrThrLysAlaLysTyrLysThr ProThrTyrProTyrLeuLeuProLysSerThrSerThrAlaAsnGlnLeuProPheThrLeuProGlyGlyGln CysThrThrValGlnValLeuArgSerValAspArgTrpSerAlaGlyThrLeuGluAsnSerIleLeuAsnAla TyrLeuHisThrIleArgGluSerGlnHisPheLeuTyrIleGluAsnGlnPhePheIleSerCysSerAspGly ArgThrValLeuAsnLysValGlyAspGluIleValAspArgIleLeuLysAlaHisLysGlnGlyTrpCysTyr ArgValTyrValLeuLeuProLeuLeuProGlyPheGluGlyAspIleSerThrGlyGlyGlyAsnSerIleGln AlaIleLeuHisPheThrTyrArgThrLeuCysArgGlyGluTyrSerIleLeuHisArgLeuLysAlaAlaMet GlyThrAlaTrpArgAspTyrIleSerIleCysGlyLeuArgThrHisGlyGluLeuGlyGlyHisProValSer GluLeuIleTyrIleHisSerLysValLeuIleAlaAspAspArgThrValIleIleGlySerAlaAsnIleAsn
```

-continued

```
AspArgSerLeuLeuGlyLysArgAspSerGluLeuAlaValLeuIleGluAspThrGluThrGluProSerLeu

MetAsnGlyAlaGluTyrGlnAlaGlySerValIleLeuGlyAlaAsnThrArgProAspLeuAspLeuArgAsp

ProIleCysAspAspPhePheGlnLeuTrpGlnAspMetAlaGluSerAsnAlaAsnIleTyrGluGlnIlePhe

ArgCysLeuProSerAsnAlaThrArgSerLeuArgThrLeuArgGluTyrValAlaValGluProLeuAlaThr

ValSerProProLeuAlaArgSerGluLeuThrGlnValGlnGlyHisLeuValHisPheProLeuLysPheLeu

GluAspGluSerLeuLeuProProLeuGlySerLysGluGlyMetIleProLeuGluValTrpThrSTP
```

Protein Sequence for hPLD2c                                                                                              (SEQ ID NO. 7)

```
MetThrAlaThrProGluSerLeuPheProThrGlyAspGluLeuAspSerSerGlnLeuGlnMetGluSerAsp

GluValAspThrLeuLysGluGlyGluAspProAlaAspArgMetHisProPheLeuAlaIleTyrGluLeuGln

SerLeuLysValHisProLeuValPheAlaProGlyValProValThrAlaGlnValValGlyThrGluArgTyr

ThrSerGlySerLysValGlyThrCysThrLeuTyrSerValArgLeuThrHisGlyAspPheSerTrpThrThr

LysLysLysTyrArgHisPheGlnGluLeuHisArgAspLeuLeuArgHisLysValLeuMetSerLeuLeuPro

LeuAlaArgPheAlaValAlaTyrSerProAlaArgAspAlaGlyAsnArgLysMetProSerLeuProArgAla

GlyProGluGlySerThrArgHisAlaAlaSerLysGlnLysTyrLeuGluAsnTyrLeuAsnGlyLeuLeuThr

MetSerPheTyrArgAsnTyrHisAlaMetThrGluPheLeuGluValSerGlnLeuSerPheIleProAspLeu

GlyArgLysGlyLeuGluGlyMetIleArgLysArgSerGlyGlyHisArgValProGlyLeuThrCysCysGly

ArgAspGlnValCysTyrArgTrpSerLysArgTrpLeuValValLysAspSerPheLeuLeuTyrMetCysLeu

GluThrGlyAlaIleSerPheValGlnLeuPheAspProGlyPheGluValGlnValGlyLysArgSerThrGlu

AlaArgHisGlyValArgIleAspThrSerHisArgSerLeuIleLeuLysCysSerSerTyrArgGlnAlaArg

TrpTrpAlaGlnGluIleThrGluLeuAlaGlnGlyProGlyArgAspPheLeuGlnLeuHisArgHisAspSer

TyrAlaProProArgProGlyThrLeuAlaArg
```

Example 4

Similarity of hPLD2 to Known PLD's

The DNA sequence and the amino acid sequence as determined in EXAMPLE 8 for human PLD2 was compared to known DNA sequences and amino acid sequences for human PLD1 and mouse and rat PLD2. The degree of alignment or similarity was determined using the Geneworks DNA Alignment and PAM-250 Scoring matrix for protein sequences. Table 1 summarizes the results of the comparison and shows that the DNA similarity to mouse (GenBank Accession #87557) and rat (GenBank Accession #D88672) PLD2 was less than 90 percent for both the DNA and amino acid sequences. The similarity of hPLD2 to hPLD1 (GenBank Accession #U38545) was about 50 percent for both DNA and amino acid sequences.

TABLE 1

Homology of hPLD2 to known mammalian PLD's.

| Sequence Compared | DNA Similarity | Protein Similarity |
|---|---|---|
| hPLD1 | 48% identity | 49% identity |
| hPLD1a* | 48% identity | 49% identity |
| hPLD1b* | 47% identity | 51% identity |
| mPLD2 | 87% identity | 88% identity |
| rPLD2 | 87% identity | 90% identity |

*PLD1a and PLD1b are splice variants of the same message.

Example 5

Expression of PLD2 in Baculovirus

The PLD2 DNA is expressed in baculovirus as described in Colley et al., (1997) Current Biology 7: 191–201.

Example 6

Expression of PLD2 in Yeast

The PLD2 DNA is expressed in the yeast strain *S. pombe* as described in Kodaki et al., (1997) Journal of Biological Chemistry 272: 11408–11413.

Example 7

Assay for PLD Activity

The PLD assay measured the release of $^3$H choline from radiolabeled PC (Steed et al. (1996) Biochemistry 35:5229–5237). Product was separated from substrate by partitioning into water from a chloroform:methanol extraction. $^3$H PC substrate was prepared by drying stock (in methanol) with argon and re-dissolving into minimal volumes of methanol (2–10 μl). After dilution with a buffer of 20 mM Tris-HCl, pH 7.0, 1.0 mM EDTA and 0.05% Triton X-100 (PLDT buffer) to a 5× concentration, the substrate was sonicated for 30 sec and used immediately. The assay was performed with 1.0 μM [methyl-$^3$H] choline L-a-PC dipalmitoyl phosphatidylcholine (0.1 μCi/assay) and enzyme with PLDT buffer added to a final volume of 50 μl using polypropylene tubes. Since the estimated Km is greater than 1 μM, PC is limiting in this assay. Unfortunately, the solubility constraints of the lipid substrate preclude the use of higher PC concentrations. Following a 2 hour incubation at 37° C., the reaction was stopped by the addition of 250 μl of water/methanol (2:3). Choline was extracted by the addition of 250 μl of chloroform followed by vigorous vortexing and centrifugation. The radioactivity in the aqueous phase (200 μl) was counted in either a Beckman LS 3801 (Beckman Instruments Columbia Md.) or Wallac 1450 Microbeta Plus (Wallac Inc., Gaithersburg Md.) liquid scintillation counter after the addition of scintillant. Preliminary experiments established that the assay was linear with time and enzyme concentration. The material was assayed using transphosphatidylation to butanol and ethanol to verify that PLD activity is being measured. Further, product material was separated using the method of Bligh and Dyer (1959) Can. J. Biochem. Physiol. 37: 911–917 and found that PA and choline were the almost exclusive products. Other assay conditions are cited in Brown et al., (1995) J. Biol. Chem. 270:14935–14943.

Example 8

Purification of PLD2

Purification of PLD2 was performed essentially as described in Steed et al. (1996) Biochemistry 35:5229–5237 and Steed and Wennogle, 1997. Alternate purification methods are found in Colley et al., (1997) Current Biology 7: 191–201. Another alternative is the use of an epitope tag such as the 6X His Tag on the FASTBAC system (baculovirus) from Life Technologies.

Baculovirus or yeast extracts are treated as follows. Yeast extracts are obtained by subjecting the yeast cells expressing PLD2 to known breakage techniques such as, for example, sonication, shearing, lysis, etc. Triton X-100 is added to a final concentration of 1.0%, the suspension stirred for 2 h, then centrifuged at 30,000×g for 2 h. The Triton X-100 extract should have a specific activity of about $10^{-4}$ pmol/min/mg protein. This material is filtered through a 0.45 micron filter and applied to a 50 mm×300 mm Waters AP glass column (Millipore Corp., Milford, Mass.) packed with Q-Sepharose Fast Flow (approximately 600 ml; Pharmacia Biotech, Piscataway, N.J.). PLD activity is eluted with a linear gradient over 60 minutes from 0 to 0.6 M NaCl in PLDT buffer at a flow rate of 15 ml/min. Fractions (15 ml) are collected and assayed for PLD activity.

Purification of PLD Activity From Yeast

Procedures for purification of PLD activity from rabbit brain membranes through Q-sepharose, GTP-agarose, and Heparin-agarose chromatography are found in Steed et al. (1996) Biochemistry 35:5229–5237. The heparin-agarose-purified material can be further purified on a mono S HR 5/5 column (Pharmacia). Heparin-agarose-purified PLD activity was dialyzed for 3 hours at room temperature against PLDT buffer for 3 hr. This material was loaded onto the mono S column at 0.5 ml/min, washed with 5 column volumes of PLDT buffer, and PLD activity was eluted with a linear gradient (20 column volumes) of 0 to 1.0 M NaCl in PLDT buffer at room temperature. The active fractions were pooled and concentrated to 0.5 ml for size fractionation chromatography.

A gel filtration chromatography step was employed both prior to and following lectin chromatography. A 20 mm×300 mm Waters AP glass column was packed with Sephacryl S300 HR (Pharmacia), equilibrated with PLDT buffer and run at 0.25 ml/min. The column was calibrated using standards obtained from Pharmacia: Blue Dextran 2,000 (to indicate void volume), Aldolase (158 kDa), Catalase (232 kDa) and Ferritin (440 kDa). PLD sample, in PLDT buffer, was concentrated to approximately 200 ml with an Amicon stirred cell concentrator using a YM100 membrane (Amicon, W. R. Grace & Co., Danvers, Mass.), injected into the column, and fractions of 4 min were collected.

PLD activity was purified on ConA-sepharose as follows: PLD purified by Q-sepharose, GTP-agarose, Heparin-agarose, and gel filtration was dialyzed against 50 mM HEPES buffer (pH 7.4) with 0.02% Triton X-100. This material was loaded onto a 5×100 mm Waters AP column (Millipore Corp., Milford Mass.) packed with ConA-sepharose (2 ml bed volume; Pharmacia Biotech., Piscataway, N.J.). PLD activity was eluted with a 5 ml gradient of either 0.0 to 2.0 M methyl a-D-glucopyranoside or 0.0 to 2.0 M NaCl at a flow rate of 0.25 m/min; 2 min fractions were collected and assayed.

Purification of PLD Activity on GTP-Agarose

Pooled Q-Sepharose fractions were further purified as follows although such further purification may not be necessary for the purification of recombinant material. Pooled Q-Sepharose fractions (240 ml, 1.9 g total protein) were dialyzed against 15 volumes of 20 mM MES (pH 6.5), with 1.0 mM EDTA, 0.05% Triton X-100 (PLDM buffer) for 4 h. The PLD activity was loaded onto a 20 mm×300 mm Waters AP glass column (bed volume 90 ml) packed with GTP-Agarose (Sigma Chemical Co., St. Louis, Mo.; cat. # G 1771). The column was washed with 2 column volumes of PLDM buffer and one column volume of PLDM buffer supplemented with 0.1 M NaCl. PLD activity was eluted with PLDM buffer with 1.0 mM UTP. The column was run at a flow rate of 1.0 ml/min and 8 min fractions were collected. Due to limited capacity of the GTP-Agarose column, no more than 10% (10–30 mg total protein per run) of the pooled PLD-containing fractions from the Q-Sepharose step was loaded at a time on the GTP-Agarose column. Samples were run on a Bio-Rad 10% mini-PROTEAN gel (Bio-Rad Laboratories, Hercules Calif.) and visualized using silver staining.

Purification of PLD Activity on Heparin-Agarose

Heparin agarose chromatography was used following Q-Sepharose or GTP-Agarose as indicated. PLD activity (5–20 mg total protein per run) was loaded onto a 5 mm×100 mm Waters AP column packed with Heparin Agarose (bed volume=2.0 ml; Sigma cat. #H-6508) and equilibrated with PLDT buffer. After washing the column with 2 volumes of PLDT buffer, PLD activity was eluted with a linear gradient from 0 to 1.0 M NaCl over 100 minutes at a flow rate of 0.25 ml/min. Fractions of 4 min were collected and the active fractions pooled. Alternatively, 200–300 mg of total protein (an entire run of pooled Q-Sepharose fractions) was purified on a 5 mm×100 mm Waters AP column (bed volume 7.0 ml) using the same gradient run at 2.0 ml/min.

Purification of PLD Activity on Sephacryl S300 HR

A 20 mm×300 mm Waters AP glass column was packed with Sephacryl S300 HR (Pharmacia) and equilibrated with PLDT buffer. The column was calibrated using standards obtained from Pharmacia: Blue Dextran 2,000 (void volume), Aldolase (158 kDa), Catalase (232 kDa) and Ferritin (440 kDa). Sample was concentrated to approximately 200 µl 0.5–5.0 mg total protein) with an Amicon stirred cell concentrator using a YM100 membrane (Amicon, W. R. Grace & Co., Danvers, Mass.) and injected into the column run at 0.25 ml/min. Fractions of 4 min were collected.

Protein Sequence Analysis

Protein sequences were determined as previously described (Aebersold, et al., (1987) Proc. Natl. Acad. Sci. U.S.A. 84, 6970–6974). Samples of approximately 5 micrograms were separated on 7.5% SDS PAGE gels and transferred to nitrocellulose using a Bio-Rad mini-transfer apparatus. Amino acid sequences were determined at the Harvard Microsequencing facility from fragments generated by in situ digestion with trypsin.

Although the present invention has been described in considerable detail with reference to certain preferred versions thereof, other versions are possible without departing from the spirit and scope of the preferred versions contained herein.

---

What is claimed is:

1. An isolated polynucleotide comprising a DNA sequence encoding a polypeptide with the amino acid sequence set forth in SEQ ID NO:2.

2. An isolated polynucleotide comprising the DNA sequence set forth in SEQ ID NO:1.

3. An isolated polynucleotide comprising the DNA sequence set out in SEQ ID NO:1 wherein bases 2588 to 2622 have been deleted.

4. An isolated polynucleotide comprising the DNA sequence of claim 2 and which further comprises the nucleotide sequence set forth in SEQ ID NO:8 inserted after base 1170 and before base 1171 of SEQ ID NO:1.

5. A method for producing a PLD2 protein comprising:
   a) inserting a DNA sequence according to claim 1 into a host cell;
   b) causing said host cell to express PLD2 protein encoded by said DNA sequence; and
   c) isolating said PLD2 protein.

6. A method for producing a PLD2 protein comprising:
   a) inserting a DNA sequence according to claim 2 into a host cell;
   b) causing said host cell to express PLD2 protein encoded by said DNA sequence; and
   c) isolating said PLD2 protein.

7. The method according to claim 5 wherein said host cell is selected from the group consisting of an insect cell, a yeast cell, and an *E. coli* cell.

8. A host cell which can be propagated in vitro and which is capable upon growth in culture of producing a polypeptide with the amino acid sequence set forth in SEQ ID NO:2, said cell comprising non-human DNA sequences which control transcription of the polynucleotide according to claim 1.

* * * * *